US005410031A

United States Patent [19]
Wright et al.

[11] Patent Number: 5,410,031
[45] Date of Patent: Apr. 25, 1995

[54] NUCLEOSIDE COTRANSPORTER PROTEIN CDNA

[75] Inventors: Ernest M. Wright, Los Angeles, Calif.; Ana M. Pajor, Tucson, Ariz.

[73] Assignee: The Regents of the University of California Office of Technology Transfer, Los Angeles, Calif.

[21] Appl. No.: 841,651

[22] Filed: Feb. 24, 1992

[51] Int. Cl.$^6$ .................... C07H 21/04; C12N 15/63; C12N 5/10
[52] U.S. Cl. .............................. 536/23.5; 435/172.3; 435/240.1
[58] Field of Search ............................ 536/27, 23.5, ; 435/172.3, 240.1

[56] References Cited

PUBLICATIONS

Williams, T. C., and S. M. Jarvis. Multiple Sodium-dependent nucleoside transport systems in bovine renal . . . Biochem J. (1991) 274:27–33.

Jarvis, S. M. and D. A. Griffith. Expression of the rabbit intestinal N2 Na+/nucleoside transporter in *Xenopus laevis* oocytes. Biochem J. (1991) 278:605–607.

Peerce and Wright, "Conformational Changes in the Intestinal Brush Border Sodium–Glucose Cotransporter Labeled with Fluorescein Isothiocyanate", *Proc. Natl. Acad. Sci.* 81:2223–2226 (1984).

Wright and Peerce, "Identification and Conformational Changes of the Intestinal Proline Carrier", *J. Biol. Chem.* 259:14993–14996 (1984).

Radian et al., "Purification and Identification of the Functional Sodium- and Chloride-coupled γ-Aminobutyric Acid Transport Glycoprotein from Rat Brain", *J. Biol. Chem.* 261:15437–15441 (1986).

Peerce and Wright, "Sodium-induced Conformational Changes in the Glucose Transporter of Intestinal Brush Borders", *J. Biol. Chem.* 259-14105–14112 (1984).

Peerce and Wright, "Evidence for Tyrosyl Residues at the Na+ Site on the Intestinal Na+/Glucose Cotransporter", *J. Biol. Chem.* 260:6026–6031 (1985).

Peerce and Wright, "Distance Between Substrate Sites on the Na-glucose Cotransporter by Fluorescence Energy Transfer", *Proc. Natl. Acad. Sci.* 83:8092–8096 (1986).

Peerce and Wright, "Examination of the Na+-Induced Conformational Change of the Intestinal Brush Border Sodium/Glucose Symporter Using Fluorescent Probes", *Biochem.* 26:4272–4279 (1987).

Hediger et al., "Expression Cloning and cDNA Sequencing of the Na+/Glucose Co-Transporter", *Nature* 330:379–381 (1987).

Coady et al., "Sequence Homologies Among Intestinal and Renal Na+/Glucose Cotransporter", *Am. J. Physiol.* 259:C605–C610 (1990).

Hediger et al., "Expression of Size-Selected mRNA Encoding the Intestinal Na/Glucose Cotransporter in *Xenopus laevis* Oocytes", *Proc. Natl. Acad. Sci.* 86:2634–2637 (1987).

Ohta et al., "Regulation of Glucose Transporters in LLC-PK$_1$ Cells: Effects of D-Glucose and Monosaccharides", *Mol. Cell. Biol.* 10:6491–6499 (1990).

Nakao et al., "Nucleotide Sequence of putP, the Proline Carrier Gene of *Escherichia coli* K12", *Mol. Gen. Genet.* 208:70–75 (1987).

Jackowski and Alix, "Cloning, Sequence, and Expression of the Pantothenate Permease (*pan F*) Gene of *Escherichia coli*", *Bacteriol.* 172:3843–3848 (1990).

(List continued on next page.)

Primary Examiner—Margaret Parr
Assistant Examiner—David Schreiber
Attorney, Agent, or Firm—Merchant, Gould, Smith, Edell, Welter & Schmidt

[57] ABSTRACT

The complete cDNA sequence encoding the amino acid sequence corresponding to mammalian Na+/nucleoside cotransporter protein (SNST) is disclosed. Methods for obtaining the gene encoding SNST and for obtaining recombinantly produced SNST are described. Antibodies, an inhibitor of nucleoside transport by SNST, and methods for detecting other inhibitors are also described. Methods for inhibiting uptake of nucleosides by SNST using the compositions of the invention are also included.

1 Claim, 7 Drawing Sheets

PUBLICATIONS

Turk et al., "Gluclose/Galactose Malabsorption Caused by a Defect in the Na+/Glucose Cotransporter", *Nature* 350:354–356 (1991).

Belardinelli et al., "The Cardiac Effects of Adenosine", *Prog. Cardiovasc. Diseases* 32:73–97 (1989).

Yarchoan and Border, "Development of Antiretroviral Therapy for the Acquired Immunodeficiency Syndrome and Related Disorders", *New Eng. J. Med.* 316:557–564 (1987).

Newey et al., "The Effect of Some Analogues of Phlorrhizin on Intestinal Hexose and Fluid Transfer", *J. Physiol.* 169:229–236 (1963).

Diedrich, "Photoaffinity-Labeling Analogs of Phlorizin and Phloretin: Synthesis and Effects on Cell Membranes", *Methods in Enzymology* 191:755–780 (1990).

Plagemann et al., "Nuceloside and Nucleobase Transport in Animal Cells", *Biochim. et Biophys. Acta* 947:405–443 (1988).

Diedrich, "The Comparative Effects of Some Phlorizin Analogs on the Renal Reabsorption of Glucose", *Biochim. et Biophys. Acta* 71:688–700 (1963).

Diedrich, "Competitive Inhibition of Intestinal Glucose Transport by Phlorizin Analogs", *Arch. Biochem. Biophys.* 117:248–256 (1966).

Lin et al., "Synthesis of Phlorizin Derivatives and Their Inhibitory Effect on the Renal Sodium/D-Glucose Cotransport System", *Biochim. et Biophys. Acta* 693:379–388 (1982).

Kozak "Comparison of Initiation of Protein Synthesis in Procaryotes, Eucaryotes, and Organelles", *Microbiol. Revs.* 47:1–45 (1983).

Deguchi et al., "Nucleotide Sequence of gltS, the Na+/Glutamate Symport Carrier Gene of *Escherichia coli* B", *J. Biol. Chem.* 265:21704–21708 (1990).

Hediger et al, "Biosynthesis of the Cloned Intestinal Na+/Glucose Cotransporter", *Biochim. et Biophys. Acta* 1064:360–364 (1991).

Yamato, "Defective Cation-Coupling Mutants of *Escherichia coli* Na+/Proline Symport Carrier", *J. Biol. Chem.* 265:2450–2455 (1990).

Lee et al., "Transport Characteristics of Renal Brush Border Na+-and K+-Dependent Uridine Carriers", *Am. J. Physiol.* 258:F1203–F1210 (1990).

Williams et al., "Characterization of Sodium-Dependent and Sodium-Independent Nucleoside Transport Systems in Rabbit Brust-Border and Basolateral Plasma-Membrane Vesicles from the Renal Outer Cortex", *Biochem.* 264:223–231 (1989).

Jarvis, "Characterization of Sodium-Dependent Nucleoside Transport in Rabbitt Intestinal Brush-Border Membrane Vesicles", *Biochim. et Biophys. Acta* 979:132–138 (1989).

FIG. 2

```
                10                    20                    30
     M E E H M E A G S R L G L G D H G A L I D N P A D I A V I A A Y F L L V I G
GTACGAATGGAGGAACACATGGAGGCAGCTCCAGACTGGGGCTGGGGGACCACGGGGCTCTCATCGACAATCCTGCTGACATCGCGGTCATTGCTGCTTATTTCCTGCTGGTCATTGGT
     10        30        50        70        90        110

40                    50                    60                    70
   V G L V S M C R T N R G T V G G Y F L A G R S M V V M P V G A S L F A S N I G S
GTCGGCTTGTGGTCCATGTGCAGAACCAACAGAGGCACCGTGGGTGGCTACTTCCTGGCAGGACGAAACATGGTGGTGGCCGGTTGGGGCCTCTCTCTTTGCTAGCAATATCGGCAGT
     130       150       170       190       210       230

80                    90                   100                   110
   G H F V G L A G T G A A N G L A V A G F E V N A L F V V L L L G V L F A P V Y L
GGCCACTTTGTGGGCCTGGCGGGGACCGGTGCTGCAAACGGCTTGGCTGTGGCTGGATTTGAGTGGAATGCGCTGTTCGTGGTGCTGCTCCTGGGTTGGCTGTTCGCGCCGGTGTACCTG
     250       270       290       310       330       350

120                   130                   140                   150
   T A G V I T M P Q Y L R K R F G G H R I R L Y L S V L S L F L Y I F T K I S V D
ACCGCAGGCGTCATTACGATGCCGCAGTACCTGCGCAAGCGCTTCGGCGGCCATCGGATCCGCCTCTACTTGTCCGTGCTCTCGCTTTTTCTGTACATCTTCACCAAGATCTCGGTGGAC
     370       390       410       430       450       470

160                   170                   180                   190
   M F S G A V F I Q Q A L G V N I Y A S V I A L L G I T M V Y T V T G G L A A L M
ATGTTCTCCGGGGCGGTGTTTATTCAGCAGGCTCTAGGCTGGAATATTTACGCTTCGGTCATCGCGCTCCTGGGCATCACCATGGTTTACACCGTGACAGGAGGCTGGCAGCGCTGATG
     490       510       530       550       570       590

200                   210                   220                   230
   Y T D T V Q T F V I I A G A F I L T G Y A F H E V G G Y S G L F D K Y M G A M T
TACACAGACACAGTGCAGACCTTTGTCATCATCGCGGGGGCCTTCATCCTCACCGGTTACGCCTTCCACGAGGTGGGCGGGTATTCCGGGCTCTTCGACAAATACATGGGAGCGATGACT
     610       630       650       670       690       710

240                   250                   260                   270
   S L T V S E D P A V G N I S S S C Y R P R D S Y H L L R D P V T G D L P V P A
TCGCTGACGGTGTCCGAGGACCCGGCTGTGGGCAACATCTCCAGCTCCTGCTACCGACCCCGGCTGACTCCTATCATCTGCTCCGGGACCCTGTGACGGGGGACCTACCATGGCCCGCG
     730       750       770       790       810       830

280                   290                   300                   310
   L L L G L T I V S G V Y V C S D Q V I V Q R C L A G R N L T H I K A G C I L C G
CTGCTCCTGGGGCTCACCATCGTCTCGGGCTGGTACTGGTGCAGTGACCAGGTCATAGTACAGCGCTGCCTGGCCGGGAGGAACCTGACCCACATCAAGGCAGGCTGCATCTTGTGTGGC
     850       870       890       910       930       950

320                   330                   340                   350
   Y L K L T P M F L M V M P G M I S R I L Y P D E V A C V A P E V C K R V C G T E
TACCTGAAGCTGACGCCCATGTTCCTCATGGTCATGCCAGGAATGATCAGCCGCATCCTTTACCCTGACGAGGTGGCCGTGCGTGGCCTGAGGTGTGTAAGCGCGTGTGGCACGGAA
     970       990       1010      1030      1050      1070
```

```
                    360                    370                    380                    390
      V  G  C  S  N  I  A  Y  P  R  L  V  V  K  L  M  P  N  G  L  R  G  L  M  L  A  V  M  L  A  A  L  M  S  S  L  A  S  I  F
     GTGGGCTGCTCCAACATCGCCTATCCGCGGCTCGTTGTGAAGCTCATGCCCAACGGTCTGCGCGGACTCATGCTGGCGGTCATGTTGGCCGCGCTCATGTCTTCGCTGGCCTCCATCTTC
         1090                 1110                 1130                 1150                 1170                 1190

400                    410                    420                    430
      N  S  S  S  T  L  F  T  M  D  I  Y  T  L  R  P  R  A  G  E  G  E  L  L  L  V  G  R  L  V  V  V  F  I  V  A  V  S  V  A
     AACAGCAGCAGCACTCTCTTCACCATGGACATCTACACGCTGCGGCCCCGCGCCGGCGAAGGCGAGCTGCTGCTAGTAGGACGGCTCTGGGTGGTGTTCATCGTGGCCGGTGTCGGTGGCC
         1210                 1230                 1250                 1270                 1290                 1310

440                    450                    460                    470
      V  L  P  V  V  Q  A  A  Q  G  G  Q  L  F  D  Y  I  Q  S  V  S  S  Y  L  A  P  P  V  S  A  V  F  V  V  A  L  F  V  P  R
     TGGCTACCTGTGGTGCAGGCGGCACAGGGCGGGCAGCTCTTCGATTACATCCAGTCCGTTTCCAGCTACTTGGCCCCGCCTGTGTCTGCAGTCTTCGTCGTGGCGCTCTTCGTGCCGCGC
         1330                 1350                 1370                 1390                 1410                 1430

480                    490                    500                    510
      V  N  E  K  G  A  F  W  G  L  I  G  G  L  L  M  G  L  A  R  L  I  P  E  F  S  F  G  T  G  S  C  V  R  P  S  A  C  P  A
     GTTAATGAGAAGGGCGCCTTCTGGGGACTGATAGGGGGCCTGCTAATGGGGCTGGCACGCCTTATTCCCGAGTTCTCCTTCGGCACGGGCAGCTGCGTGCGACCCTCTGCTTGCCCGGCA
         1450                 1470                 1490                 1510                 1530                 1550

520                    530                    540                    550
      F  L  C  R  V  H  Y  L  Y  F  A  I  V  L  F  F  C  S  G  L  L  I  I  I  V  S  L  C  T  A  P  I  P  R  K  H  L  H  R  L
     TTCCTGTGTCGGGTGCACTACCTCTACTTCGCCATTGTGCTCTTCTTCTGCTCTGGCCTCCTCATCATCATCGTCTCCTTGTGCACTGCACCCATCCCACGCAAGCACCTCCACCGCCTG
         1570                 1590                 1610                 1630                 1650                 1670

560                    570                    580                    590
      V  F  S  L  R  H  S  K  E  E  R  E  D  L  D  A  D  E  L  E  A  P  A  S  P  P  V  Q  N  G  R  P  E  H  A  V  E  M  E  E
     GTTTTCAGTCTCCGGCACAGCAAGGAGGAACGGGAAGACCTGGATGCTGACGAGCTGGAAGCCCCGGCCTCTCCCCCTGTCCAGAATGGGCGCCCAGAGCACGCAGTGGAGATGGAAGAG
         1690                 1710                 1730                 1750                 1770                 1790

600                    610                    620                    630
      P  Q  A  P  G  P  G  L  F  R  Q  C  L  L  V  F  C  G  N  M  R  G  R  A  G  G  P  A  P  P  T  Q  E  E  E  A  A  A  A  R
     CCCCAGGCCCCGGGCCCAGGCCTGTTCCGCCAGTGCTTGCTGGTTCTGTGGAATGAACAGGGGCAGGGCAGGTGGCCCCGCACCCCCTACCCAGGAGGAGGAGGCTGCAGCGGCCAGG
         1810                 1830                 1850                 1870                 1890                 1910

640                    650                    660                    670
      R  L  E  D  I  N  E  D  P  R  V  S  R  V  V  N  L  N  A  L  L  N  M  A  V  A  M  F  F  V  G  F  Y  A
     CGGCTGGAGGACATCAACGAGGACCCGCGCGTGGTCCCGGGTGGTCAACCTCAATGCCCTGCTCATGATGGCCGTGGCCATGTTTTTCTGGGGCTTTTATGCCTAGGGCCGACTGTGTTGG
         1930                 1950                 1970                 1990                 2010                 2030

GCATCACGAGCCACAGGTCAGGACAGGGCTGGCCGCACAATGAGCAGGGATCAGGAGCCTGCAGCGGTCCCCGGAAAGGGGGAAGGGCAGGAGTGGTATGGGAAGCCCAGTCCATTTG
         2050                 2070                 2090                 2110                 2130                 2150

ATTGGCAGTCACTTGCACGAGGCCTCAGCCAAGCTGCCCTAACGTTTCCCTCAGCAAAAATAAAGCAGCCGTTCCCCC  (SEQ  ID  NO: 1)
         2170                 2190                 2210          2230
```

```
  1 MEEHMEAG..SRLGLGDHGAL.....IDNPADIAVIAAYFLLVIGVGLWS  43
    |: :  ||  : ::|      | |:||| ||  |||:|::||||
  1 ....MDSSTLSPLTTSTAAPLESYERIRNAADISVIVIYFLVVMAVGLWA  46

44 MCRTNRGTVGGYFLAGRSMVWWPVGASLFASNIGSGHFVGLAGTGAANGL  93
    |  ||||||||:||||||||||:|||||||||||||||||||||||| |:
 47 MFSTNRGTVGGFFLAGRSMVWWPIGASLFASNIGSGHFVGLAGTGAASGI  96

94 AVAGFEWNALFVVLLLGWLFAPVYLTAGVITMPQYLRKRFGGHRIRLYLS  143
    | :|||||||::|::|||:| |:|: |||:|||:|| ||||| || :|||
 97 ATGGFEWNALIMVVVLGWVFVPIYIRAGVVTMPEYLQKRFGGKRIQIYLS  146

144 VLSLFLYIFTKISVDMFSGAVFIQQALGWNIYASVIALLGITMVYTVTGG  193
    :|||:|||||||| |:||||:||| ||::||  :| || || :||:|||
147 ILSLLLYIFTKISADIFSGAIFIQLTLGLDIYVAIIILLVITGLYTITGG  196

194 LAALMYTDTVQTFVIIAGAFILTGYAFHEVGGYSGLFDKYMGAMTSLTVS  243
    |||::||||:||  :::  |   ||||:|||||||| :: :||| |: |
197 LAAVIYTDTLQTAIMMVGSVILTGFAFHEVGGYEAFTEKYMRAIPSQISY  246

244 EDPAVGNISSSCYRPRPDSYHLLRDPVTGDLPWPALLLGLTIVSGWYWCS  293
    ::    |   || || | :|::||::|||:|||:|::|: |:  ||||
247 GN...TSIPQKCYTPREDAFHIFRDAITGDIPWPGLVFGMSILTLWYWCT  293

294 DQVIVQRCLAGRMLTHIKAGCILCGYLKLTPMFLMVMPGMISRILYPDEV  343
    ||||||||| ::||  |:|||||||||||:  ||||:|| |:|||||  |  | |
294 DQVIVQRCLSAKNLSHVKAGCILCGYLKVMPMFLIVMMGMVSRILYTDKV  343
```

```
344 ACVAPEVCKRVCGTEVGCSNIAYPRLVVKLMPNGLRGLMLAVMLAALMSS 393
    ||| | | ||| ||| |||:| ||| |||||||||| ||:| ||||
344 ACVVPSECERYCGTRVGCTNIAFPTLVVELMPNGLRGLMLSVMMASLMSS 393

394 LASIFNSSSTLFTMDIYT.LRPRAGEGELLLVGRLWVVFIVAVSVAWLPV 442
    |.|||||  |||||||||| :| :|:| ||:: |||:::|::::|:||:|:
394 LTSIFNSASTLFTMDIYTKIRKKASEKELMIAGRLFMLFLIGISIAWVPI 443

443 VQAAQGGQLFDYIQSVSSYLAPPVSAVFVVALFVPRVNEKGAFWGLIGGL 492
    || ||:|||||||||: |||:|| |||::|:| |||| ||||||: |:
444 VQSAQSGQLFDYIQSITSYLGPPIAAVFLLAIFWKRVNEPGAFWGLVLGF 493

493 LMGLARLIPEFSFGTGSCVRPSACPAFLCRVHYLYFAIVLFFCSGLLIII 542
    |:|: |:| || :|||||: || || ::| ||||||||:|| | : :::
494 LIGISRMITEFAYGTGSCMEPSNCPTIICGVHYLYFAIILFVISIITVVV 543

543 VSLCTAPIPRKHLHRLVFSLRHSKEEREDLDADELEAPASPPVQNGRPEH 592
    ||| | ||| || || :|||:||||| ||||:| :         ||
544 VSLFTKPIPDVHLYRLCWSLRNSKEERIDLDAGEEDIQEA.......PEE 586

593 AVEMEEPQAPGPGLFRQCLLWFCGMNRGRAGGPAPPTQEEEAAAARRLED 642
    | :|| |:||  :|||:: :::  : |||||| :|  |
587 ATDTEVPKKK.KGFFRRAYDLFCGLDQDKG...PKMTKEEEAAMKLKLTD 632

643 INEDPRWSRVVNLNALLMMAVAMFFWGFYA 672 (SEQ ID NO:3)
    ||| ||||:|:::::|||:| :::::|
633 TSEHPLWRTVVNINGVILLAVAVFCYAYFA 662 (SEQ ID NO:4)
```

FIG. 3 CONTINUED

FIG. 4
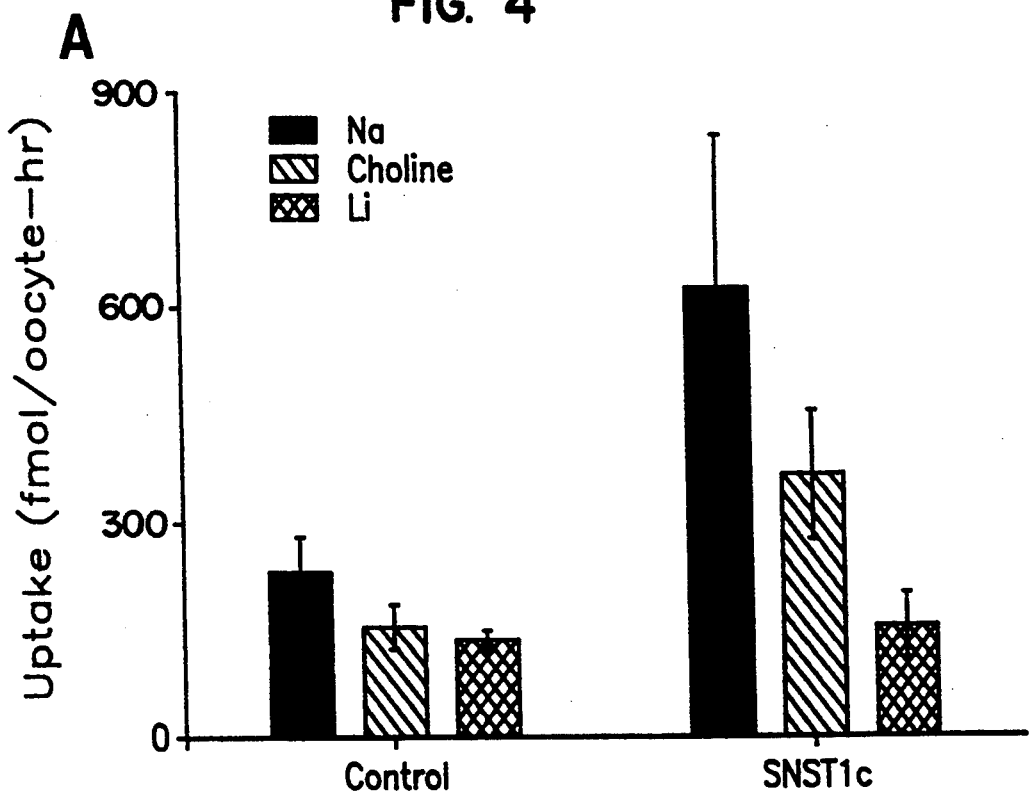
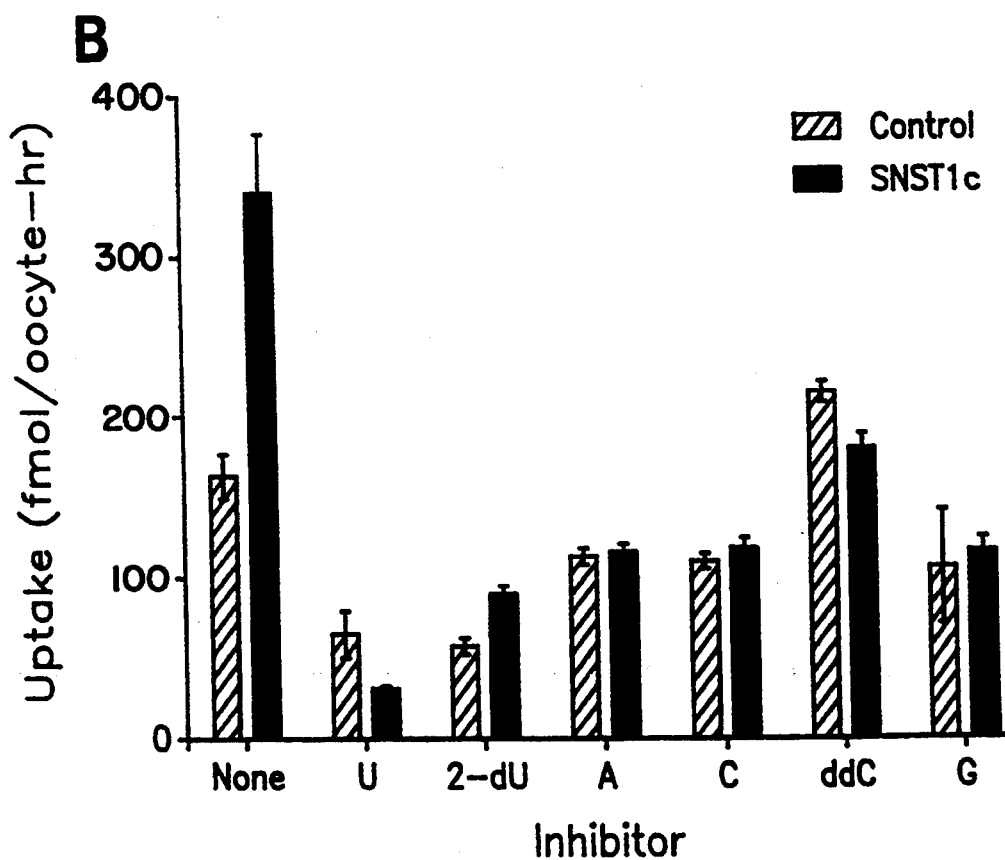

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 2238 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Oryctolagus cuniculus (ix) FEATURE:
        (A) NAME/KEY: CDS
        (B) LOCATION: 7..2022

(xi) SEQUENCE DESCRIPTION: SEQ ID NO:1:

```
GTACGA ATG GAG GAA CAC ATG GAG GCA GGC TCC AGA CTG GGG CTG GGG        48
       Met Glu Glu His Met Glu Ala Gly Ser Arg Leu Gly Leu Gly
        1               5                      10

GAC CAC GGG GCT CTC ATC GAC AAT CCT GCT GAC ATC GCG GTC ATT GCT        96
Asp His Gly Ala Leu Ile Asp Asn Pro Ala Asp Ile Ala Val Ile Ala
 15              20                  25                  30

GCT TAT TTC CTG CTG GTC ATT GGT GTC GGC TTG TGG TCC ATG TGC AGA       144
Ala Tyr Phe Leu Leu Val Ile Gly Val Gly Leu Trp Ser Met Cys Arg
                35                  40                  45

ACC AAC AGA GGC ACC GTG GGT GGC TAC TTC CTG GCA GGA CGA AGC ATG       192
Thr Asn Arg Gly Thr Val Gly Gly Tyr Phe Leu Ala Gly Arg Ser Met
            50                  55                  60

GTG TGG TGG CCG GTT GGG GCC TCT CTC TTT GCT AGC AAT ATC GGC AGT       240
Val Trp Trp Pro Val Gly Ala Ser Leu Phe Ala Ser Asn Ile Gly Ser
        65                  70                  75

GGC CAC TTT GTG GGC CTG GCG GGG ACC GGT GCT GCA AAC GGC TTG GCT       288
Gly His Phe Val Gly Leu Ala Gly Thr Gly Ala Ala Asn Gly Leu Ala
    80                  85                  90

GTG GCT GGA TTT GAG TGG AAT GCG CTG TTC GTG GTG CTG CTC CTG GGT       336
Val Ala Gly Phe Glu Trp Asn Ala Leu Phe Val Val Leu Leu Leu Gly
 95                 100                 105                 110

TGG CTG TTC GCG CCG GTG TAC CTG ACC GCA GGC GTC ATT ACG ATG CCG       384
Trp Leu Phe Ala Pro Val Tyr Leu Thr Ala Gly Val Ile Thr Met Pro
                115                 120                 125

CAG TAC CTG CGC AAG CGC TTC GGC GGC CAT CGG ATC CGC CTC TAC TTG       432
Gln Tyr Leu Arg Lys Arg Phe Gly Gly His Arg Ile Arg Leu Tyr Leu
            130                 135                 140

TCC GTG CTC TCG CTT TTT CTG TAC ATC TTC ACC AAG ATC TCG GTG GAC       480
Ser Val Leu Ser Leu Phe Leu Tyr Ile Phe Thr Lys Ile Ser Val Asp
        145                 150                 155

ATG TTC TCC GGG GCG GTG TTT ATT CAG CAG GCT CTA GGC TGG AAT ATT       528
Met Phe Ser Gly Ala Val Phe Ile Gln Gln Ala Leu Gly Trp Asn Ile
    160                 165                 170
```

| | | | | | | | | | | | | | | | | |
|---|---|---|---|---|---|---|---|---|---|---|---|---|---|---|---|---|
| TAC | GCT | TCG | GTC | ATC | GCG | CTC | CTG | GGC | ATC | ACC | ATG | GTT | TAC | ACC | GTG | 576 |
| Tyr 175 | Ala | Ser | Val | Ile 180 | Ala | Leu | Leu | Gly | Ile 185 | Thr | Met | Val | Tyr | Thr 190 | Val | |
| ACA | GGA | GGG | CTG | GCA | GCG | CTG | ATG | TAC | ACA | GAC | ACA | GTG | CAG | ACC | TTT | 624 |
| Thr | Gly | Gly | Leu | Ala 195 | Ala | Leu | Met | Tyr | Thr 200 | Asp | Thr | Val | Gln | Thr 205 | Phe | |
| GTC | ATC | ATC | GCG | GGG | GCC | TTC | ATC | CTC | ACC | GGT | TAC | GCC | TTC | CAC | GAG | 672 |
| Val | Ile | Ile | Ala 210 | Gly | Ala | Phe | Ile | Leu 215 | Thr | Gly | Tyr | Ala | Phe 220 | His | Glu | |
| GTG | GGC | GGG | TAT | TCC | GGG | CTC | TTC | GAC | AAA | TAC | ATG | GGA | GCG | ATG | ACT | 720 |
| Val | Gly | Gly 225 | Tyr | Ser | Gly | Leu | Phe 230 | Asp | Lys | Tyr | Met | Gly 235 | Ala | Met | Thr | |
| TCG | CTG | ACG | GTG | TCC | GAG | GAC | CCG | GCT | GTG | GGC | AAC | ATC | TCC | AGC | TCC | 768 |
| Ser | Leu 240 | Thr | Val | Ser | Glu | Asp 245 | Pro | Ala | Val | Gly | Asn 250 | Ile | Ser | Ser | Ser | |
| TGC | TAC | CGA | CCC | CGG | CCT | GAC | TCC | TAT | CAT | CTG | CTC | CGG | GAC | CCT | GTG | 816 |
| Cys 255 | Tyr | Arg | Pro | Arg | Pro 260 | Asp | Ser | Tyr | His | Leu 265 | Leu | Arg | Asp | Pro | Val 270 | |
| ACG | GGG | GAC | CTA | CCA | TGG | CCC | GCG | CTG | CTC | CTG | GGG | CTC | ACC | ATC | GTC | 864 |
| Thr | Gly | Asp | Leu | Pro 275 | Trp | Pro | Ala | Leu | Leu 280 | Leu | Gly | Leu | Thr | Ile 285 | Val | |
| TCG | GGC | TGG | TAC | TGG | TGC | AGT | GAC | CAG | GTC | ATA | GTA | CAG | CGC | TGC | CTG | 912 |
| Ser | Gly | Trp | Tyr 290 | Trp | Cys | Ser | Asp | Gln 295 | Val | Ile | Val | Gln | Arg 300 | Cys | Leu | |
| GCC | GGG | AGG | AAC | CTG | ACC | CAC | ATC | AAG | GCA | GGC | TGC | ATC | TTG | TGT | GGC | 960 |
| Ala | Gly | Arg 305 | Asn | Leu | Thr | His | Ile 310 | Lys | Ala | Gly | Cys | Ile 315 | Leu | Cys | Gly | |
| TAC | CTG | AAG | CTG | ACG | CCC | ATG | TTC | CTC | ATG | GTC | ATG | CCA | GGA | ATG | ATC | 1008 |
| Tyr | Leu 320 | Lys | Leu | Thr | Pro 325 | Met | Phe | Leu | Met | Val 330 | Met | Pro | Gly | Met | Ile | |
| AGC | CGC | ATC | CTT | TAC | CCT | GAC | GAG | GTG | GCG | TGC | GTG | GCG | CCT | GAG | GTG | 1056 |
| Ser 335 | Arg | Ile | Leu | Tyr | Pro 340 | Asp | Glu | Val | Ala | Cys 345 | Val | Ala | Pro | Glu | Val 350 | |
| TGT | AAG | CGC | GTG | TGT | GGC | ACG | GAA | GTG | GGC | TGC | TCC | AAC | ATC | GCC | TAT | 1104 |
| Cys | Lys | Arg | Val | Cys 355 | Gly | Thr | Glu | Val | Gly 360 | Cys | Ser | Asn | Ile | Ala 365 | Tyr | |
| CCG | CGG | CTC | GTT | GTG | AAG | CTC | ATG | CCC | AAC | GGT | CTG | CGC | GGA | CTC | ATG | 1152 |
| Pro | Arg | Leu | Val 370 | Val | Lys | Leu | Met | Pro 375 | Asn | Gly | Leu | Arg | Gly 380 | Leu | Met | |
| CTG | GCG | GTC | ATG | TTG | GCC | GCG | CTC | ATG | TCT | TCG | CTG | GCC | TCC | ATC | TTC | 1200 |
| Leu | Ala | Val | Met 385 | Leu | Ala | Ala | Leu | Met 390 | Ser | Ser | Leu | Ala | Ser 395 | Ile | Phe | |
| AAC | AGC | AGC | AGC | ACT | CTC | TTC | ACC | ATG | GAC | ATC | TAC | ACG | CTG | CGG | CCC | 1248 |
| Asn | Ser 400 | Ser | Ser | Thr | Leu | Phe 405 | Thr | Met | Asp | Ile | Tyr 410 | Thr | Leu | Arg | Pro | |
| CGC | GCC | GGC | GAA | GGC | GAG | CTG | CTG | CTA | GTA | GGA | CGG | CTC | TGG | GTG | GTG | 1296 |
| Arg 415 | Ala | Gly | Glu | Gly | Glu 420 | Leu | Leu | Leu | Val | Gly 425 | Arg | Leu | Trp | Val | Val 430 | |
| TTC | ATC | GTG | GCG | GTG | TCG | GTG | GCC | TGG | CTA | CCT | GTG | GTG | CAG | GCG | GCA | 1344 |
| Phe | Ile | Val | Ala | Val 435 | Ser | Val | Ala | Trp | Leu 440 | Pro | Val | Val | Gln | Ala 445 | Ala | |
| CAG | GGC | GGG | CAG | CTC | TTC | GAT | TAC | ATC | CAG | TCC | GTT | TCC | AGC | TAC | TTG | 1392 |
| Gln | Gly | Gly | Gln | Leu 450 | Phe | Asp | Tyr | Ile | Gln 455 | Ser | Val | Ser | Ser | Tyr 460 | Leu | |
| GCC | CCG | CCT | GTG | TCT | GCA | GTC | TTC | GTC | GTG | GCG | CTC | TTC | GTG | CCG | CGC | 1440 |
| Ala | Pro | Pro | Val 465 | Ser | Ala | Val | Phe | Val 470 | Val | Ala | Leu | Phe | Val 475 | Pro | Arg | |
| GTT | AAT | GAG | AAG | GGC | GCC | TTC | TGG | GGA | CTG | ATA | GGG | GGC | CTG | CTA | ATG | 1488 |
| Val | Asn | Glu | Lys 480 | Gly | Ala | Phe | Trp | Gly 485 | Leu | Ile | Gly | Gly | Leu 490 | Leu | Met | |
| GGC | CTG | GCA | CGC | CTT | ATT | CCC | GAG | TTC | TCC | TTC | GGC | ACG | GGC | AGC | TGC | 1536 |

|     |     |     |     |     |     |     |     |     |     |     |     |     |     |     |     |
|-----|-----|-----|-----|-----|-----|-----|-----|-----|-----|-----|-----|-----|-----|-----|-----|
| Gly | Leu | Ala | Arg | Leu | Ile | Pro | Glu | Phe | Ser | Phe | Gly | Thr | Gly | Ser | Cys |
| 495 |     |     |     |     | 500 |     |     |     | 505 |     |     |     |     | 510 |     |

| GTG | CGA | CCC | TCT | GCT | TGC | CCG | GCA | TTC | CTG | TGT | CGG | GTG | CAC | TAC | CTC | 1584 |
|-----|-----|-----|-----|-----|-----|-----|-----|-----|-----|-----|-----|-----|-----|-----|-----|------|
| Val | Arg | Pro | Ser | Ala | Cys | Pro | Ala | Phe | Leu | Cys | Arg | Val | His | Tyr | Leu |      |
|     |     |     |     | 515 |     |     |     |     | 520 |     |     |     |     | 525 |     |      |

| TAC | TTC | GCC | ATT | GTG | CTC | TTC | TTC | TGC | TCT | GGC | CTC | CTC | ATC | ATC | ATC | 1632 |
| Tyr | Phe | Ala | Ile | Val | Leu | Phe | Phe | Cys | Ser | Gly | Leu | Leu | Ile | Ile | Ile |      |
|     |     |     | 530 |     |     |     |     | 535 |     |     |     |     | 540 |     |     |      |

| GTC | TCC | TTG | TGC | ACT | GCA | CCC | ATC | CCA | CGC | AAG | CAC | CTC | CAC | CGC | CTG | 1680 |
| Val | Ser | Leu | Cys | Thr | Ala | Pro | Ile | Pro | Arg | Lys | His | Leu | His | Arg | Leu |      |
|     |     | 545 |     |     |     |     | 550 |     |     |     |     | 555 |     |     |     |      |

| GTT | TTC | AGT | CTC | CGG | CAC | AGC | AAG | GAG | GAA | CGG | GAA | GAC | CTG | GAT | GCT | 1728 |
| Val | Phe | Ser | Leu | Arg | His | Ser | Lys | Glu | Glu | Arg | Glu | Asp | Leu | Asp | Ala |      |
|     |     | 560 |     |     |     |     | 565 |     |     |     |     | 570 |     |     |     |      |

| GAC | GAG | CTG | GAA | GCC | CCG | GCC | TCT | CCC | CCT | GTC | CAG | AAT | GGG | CGC | CCA | 1776 |
| Asp | Glu | Leu | Glu | Ala | Pro | Ala | Ser | Pro | Pro | Val | Gln | Asn | Gly | Arg | Pro |      |
| 575 |     |     |     |     | 580 |     |     |     |     | 585 |     |     |     |     | 590 |      |

| GAG | CAC | GCA | GTG | GAG | ATG | GAA | GAG | CCC | CAG | GCC | CCG | GGC | CCA | GGC | CTG | 1824 |
| Glu | His | Ala | Val | Glu | Met | Glu | Glu | Pro | Gln | Ala | Pro | Gly | Pro | Gly | Leu |      |
|     |     |     |     | 595 |     |     |     |     | 600 |     |     |     |     | 605 |     |      |

| TTC | CGC | CAG | TGC | TTG | CTG | TGG | TTC | TGT | GGA | ATG | AAC | AGG | GGC | AGG | GCA | 1872 |
| Phe | Arg | Gln | Cys | Leu | Leu | Trp | Phe | Cys | Gly | Met | Asn | Arg | Gly | Arg | Ala |      |
|     |     |     | 610 |     |     |     |     | 615 |     |     |     |     | 620 |     |     |      |

| GGT | GGC | CCC | GCA | CCC | CCT | ACC | CAG | GAG | GAG | GAG | GCT | GCA | GCG | GCC | AGG | 1920 |
| Gly | Gly | Pro | Ala | Pro | Pro | Thr | Gln | Glu | Glu | Glu | Ala | Ala | Ala | Ala | Arg |      |
|     |     | 625 |     |     |     |     | 630 |     |     |     |     | 635 |     |     |     |      |

| CGG | CTG | GAG | GAC | ATC | AAC | GAG | GAC | CCG | CGC | TGG | TCC | CGG | GTG | GTC | AAC | 1968 |
| Arg | Leu | Glu | Asp | Ile | Asn | Glu | Asp | Pro | Arg | Trp | Ser | Arg | Val | Val | Asn |      |
|     | 640 |     |     |     |     | 645 |     |     |     |     | 650 |     |     |     |     |      |

| CTC | AAT | GCC | CTG | CTC | ATG | ATG | GCC | GTG | GCC | ATG | TTT | TTC | TGG | GGC | TTT | 2016 |
| Leu | Asn | Ala | Leu | Leu | Met | Met | Ala | Val | Ala | Met | Phe | Phe | Trp | Gly | Phe |      |
| 655 |     |     |     |     | 660 |     |     |     |     | 665 |     |     |     |     | 670 |      |

| TAT | GCC | TAGGGCCGAC | TGTGTTGGGC | ATCACGAGCC | ACAGGTCAGG | ACAGGGCTGG | 2072 |
| Tyr | Ala |            |            |            |            |            |      |

| CCGCACAATG | AGCAGGGATC | AGGAGCCTGC | AGCGGTCCCC | GGAAAGGGGG | AAGGGGCAGG | 2132 |

| AGTGGTATGG | GAAGGCCCAG | TCCATTTGAT | TGGCAGTCAC | TTGCACGAGG | CCTCAGCCAA | 2192 |

| GCTGCCCTAA | CGTTTCCCTC | AGCAAAAATA | AAGCAGCCGT | TCCCCC |     | 2238 |

( 2 ) INFORMATION FOR SEQ ID NO:2:

( i ) SEQUENCE CHARACTERISTICS:
        ( A ) LENGTH: 672 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Glu | Glu | His | Met | Glu | Ala | Gly | Ser | Arg | Leu | Gly | Leu | Gly | Asp | His |
| 1   |     |     |     | 5   |     |     |     |     | 10  |     |     |     |     | 15  |     |

| Gly | Ala | Leu | Ile | Asp | Asn | Pro | Ala | Asp | Ile | Ala | Val | Ile | Ala | Ala | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Leu | Leu | Val | Ile | Gly | Val | Gly | Leu | Trp | Ser | Met | Cys | Arg | Thr | Asn |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Arg | Gly | Thr | Val | Gly | Gly | Tyr | Phe | Leu | Ala | Gly | Arg | Ser | Met | Val | Trp |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Trp | Pro | Val | Gly | Ala | Ser | Leu | Phe | Ala | Ser | Asn | Ile | Gly | Ser | Gly | His |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Phe | Val | Gly | Leu | Ala | Gly | Thr | Gly | Ala | Ala | Asn | Gly | Leu | Ala | Val | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

-continued

| | | | | | | | | | | | | | |
|---|---|---|---|---|---|---|---|---|---|---|---|---|---|
| Gly | Phe | Glu | Trp 100 | Asn | Ala | Leu | Phe 105 | Val | Val | Leu | Leu | Leu 110 | Gly | Trp | Leu |
| Phe | Ala | Pro 115 | Val | Tyr | Leu | Thr | Ala 120 | Gly | Val | Ile | Thr | Met 125 | Pro | Gln | Tyr |
| Leu | Arg 130 | Lys | Arg | Phe | Gly 135 | Gly | His | Arg | Ile | Arg 140 | Leu | Tyr | Leu | Ser | Val |
| Leu 145 | Ser | Leu | Phe | Leu | Tyr 150 | Ile | Phe | Thr | Lys | Ile 155 | Ser | Val | Asp | Met | Phe 160 |
| Ser | Gly | Ala | Val | Phe 165 | Ile | Gln | Gln | Ala | Leu 170 | Gly | Trp | Asn | Ile | Tyr 175 | Ala |
| Ser | Val | Ile | Ala 180 | Leu | Leu | Gly | Ile | Thr 185 | Met | Val | Tyr | Thr | Val 190 | Thr | Gly |
| Gly | Leu | Ala 195 | Ala | Leu | Met | Tyr | Thr 200 | Asp | Thr | Val | Gln | Thr 205 | Phe | Val | Ile |
| Ile | Ala 210 | Gly | Ala | Phe | Ile | Leu 215 | Thr | Gly | Tyr | Ala | Phe 220 | His | Glu | Val | Gly |
| Gly 225 | Tyr | Ser | Gly | Leu | Phe 230 | Asp | Lys | Tyr | Met | Gly 235 | Ala | Met | Thr | Ser | Leu 240 |
| Thr | Val | Ser | Glu | Asp 245 | Pro | Ala | Val | Gly | Asn 250 | Ile | Ser | Ser | Ser 255 | Cys | Tyr |
| Arg | Pro | Arg | Pro 260 | Asp | Ser | Tyr | His | Leu 265 | Leu | Arg | Asp | Pro 270 | Val | Thr | Gly |
| Asp | Leu | Pro 275 | Trp | Pro | Ala | Leu | Leu 280 | Leu | Gly | Leu | Thr | Ile 285 | Val | Ser | Gly |
| Trp | Tyr 290 | Trp | Cys | Ser | Asp | Gln 295 | Val | Ile | Val | Gln | Arg 300 | Cys | Leu | Ala | Gly |
| Arg 305 | Asn | Leu | Thr | His | Ile 310 | Lys | Ala | Gly | Cys | Ile 315 | Leu | Cys | Gly | Tyr | Leu 320 |
| Lys | Leu | Thr | Pro | Met 325 | Phe | Leu | Met | Val 330 | Met | Pro | Gly | Met | Ile 335 | Ser | Arg |
| Ile | Leu | Tyr | Pro 340 | Asp | Glu | Val | Ala | Cys 345 | Val | Ala | Pro | Glu | Val 350 | Cys | Lys |
| Arg | Val | Cys 355 | Gly | Thr | Glu | Val | Gly 360 | Cys | Ser | Asn | Ile | Ala 365 | Tyr | Pro | Arg |
| Leu | Val 370 | Val | Lys | Leu | Met | Pro 375 | Asn | Gly | Leu | Arg | Gly 380 | Leu | Met | Leu | Ala |
| Val 385 | Met | Leu | Ala | Ala | Leu 390 | Met | Ser | Ser | Leu | Ala 395 | Ser | Ile | Phe | Asn | Ser 400 |
| Ser | Ser | Thr | Leu | Phe 405 | Thr | Met | Asp | Ile | Tyr 410 | Thr | Leu | Arg | Pro | Arg 415 | Ala |
| Gly | Glu | Gly | Glu 420 | Leu | Leu | Leu | Val | Gly 425 | Arg | Leu | Trp | Val | Val 430 | Phe | Ile |
| Val | Ala | Val 435 | Ser | Val | Ala | Trp | Leu 440 | Pro | Val | Val | Gln | Ala 445 | Ala | Gln | Gly |
| Gly | Gln 450 | Leu | Phe | Asp | Tyr | Ile 455 | Gln | Ser | Val | Ser | Ser 460 | Tyr | Leu | Ala | Pro |
| Pro 465 | Val | Ser | Ala | Val | Phe 470 | Val | Val | Ala | Leu | Phe 475 | Val | Pro | Arg | Val | Asn 480 |
| Glu | Lys | Gly | Ala | Phe 485 | Trp | Gly | Leu | Ile | Gly 490 | Gly | Leu | Leu | Met | Gly 495 | Leu |
| Ala | Arg | Leu | Ile 500 | Pro | Glu | Phe | Ser | Phe 505 | Gly | Thr | Gly | Ser | Cys 510 | Val | Arg |
| Pro | Ser | Ala 515 | Cys | Pro | Ala | Phe | Leu 520 | Cys | Arg | Val | His | Tyr 525 | Leu | Tyr | Phe |
| Ala | Ile | Val | Leu | Phe | Phe | Cys | Ser | Gly | Leu | Leu | Ile | Ile | Ile | Val | Ser |

```
                530                          535                         540
Leu Cys Thr Ala Pro Ile Pro Arg Lys His Leu His Arg Leu Val Phe
545                 550             555                         560

Ser Leu Arg His Ser Lys Glu Glu Arg Glu Asp Leu Asp Ala Asp Glu
                565             570                 575

Leu Glu Ala Pro Ala Ser Pro Pro Val Gln Asn Gly Arg Pro Glu His
            580             585                 590

Ala Val Glu Met Glu Glu Pro Gln Ala Pro Gly Pro Gly Leu Phe Arg
        595             600             605

Gln Cys Leu Leu Trp Phe Cys Gly Met Asn Arg Gly Arg Ala Gly Gly
    610             615                 620

Pro Ala Pro Pro Thr Gln Glu Glu Glu Ala Ala Ala Ala Arg Arg Leu
625             630             635                         640

Glu Asp Ile Asn Glu Asp Pro Arg Trp Ser Arg Val Val Asn Leu Asn
                645             650                 655

Ala Leu Leu Met Met Ala Val Ala Met Phe Phe Trp Gly Phe Tyr Ala
            660             665                 670
```

(2) INFORMATION FOR SEQ ID NO:3:

(i) SEQUENCE CHARACTERISTICS:
        (A) LENGTH: 672 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Oryctolagus cuniculus (xi) SEQUENCE DESCRIPTION: SEQ ID NO:3:

```
Met Glu Glu His Met Glu Ala Gly Ser Arg Leu Gly Leu Gly Asp His
1               5                   10                  15

Gly Ala Leu Ile Asp Asn Pro Ala Asp Ile Ala Val Ile Ala Ala Tyr
            20                  25                  30

Phe Leu Leu Val Ile Gly Val Gly Leu Trp Ser Met Cys Arg Thr Asn
        35                  40                  45

Arg Gly Thr Val Gly Gly Tyr Phe Leu Ala Gly Arg Ser Met Val Trp
    50                  55                  60

Trp Pro Val Gly Ala Ser Leu Phe Ala Ser Asn Ile Gly Ser Gly His
65                  70                  75                  80

Phe Val Gly Leu Ala Gly Thr Gly Ala Ala Asn Gly Leu Ala Val Ala
                85                  90                  95

Gly Phe Glu Trp Asn Ala Leu Phe Val Val Leu Leu Leu Gly Trp Leu
            100                 105                 110

Phe Ala Pro Val Tyr Leu Thr Ala Gly Val Ile Thr Met Pro Gln Tyr
        115                 120                 125

Leu Arg Lys Arg Phe Gly Gly His Arg Ile Arg Leu Tyr Leu Ser Val
    130                 135                 140

Leu Ser Leu Phe Leu Tyr Ile Phe Thr Lys Ile Ser Val Asp Met Phe
145                 150                 155                 160

Ser Gly Ala Val Phe Ile Gln Gln Ala Leu Gly Trp Asn Ile Tyr Ala
                165                 170                 175

Ser Val Ile Ala Leu Leu Gly Ile Thr Met Val Tyr Thr Val Thr Gly
            180                 185                 190

Gly Leu Ala Ala Leu Met Tyr Thr Asp Thr Val Gln Thr Phe Val Ile
        195                 200                 205
```

| | | | | | | | | | | | | | | |
|---|---|---|---|---|---|---|---|---|---|---|---|---|---|---|
| Ile | Ala | Gly | Ala | Phe | Ile | Leu | Thr | Gly | Tyr | Ala | Phe | His | Glu | Val | Gly |
| | 210 | | | | 215 | | | | | 220 | | | | | |
| Gly | Tyr | Ser | Gly | Leu | Phe | Asp | Lys | Tyr | Met | Gly | Ala | Met | Thr | Ser | Leu |
| 225 | | | | | 230 | | | | | 235 | | | | | 240 |
| Thr | Val | Ser | Glu | Asp | Pro | Ala | Val | Gly | Asn | Ile | Ser | Ser | Ser | Cys | Tyr |
| | | | | 245 | | | | | 250 | | | | | 255 | |
| Arg | Pro | Arg | Pro | Asp | Ser | Tyr | His | Leu | Leu | Arg | Asp | Pro | Val | Thr | Gly |
| | | | 260 | | | | | 265 | | | | | 270 | | |
| Asp | Leu | Pro | Trp | Pro | Ala | Leu | Leu | Leu | Gly | Leu | Thr | Ile | Val | Ser | Gly |
| | | 275 | | | | | 280 | | | | | 285 | | | |
| Trp | Tyr | Trp | Cys | Ser | Asp | Gln | Val | Ile | Val | Gln | Arg | Cys | Leu | Ala | Gly |
| | 290 | | | | | 295 | | | | | 300 | | | | |
| Arg | Asn | Leu | Thr | His | Ile | Lys | Ala | Gly | Cys | Ile | Leu | Cys | Gly | Tyr | Leu |
| 305 | | | | | 310 | | | | | 315 | | | | | 320 |
| Lys | Leu | Thr | Pro | Met | Phe | Leu | Met | Val | Met | Pro | Gly | Met | Ile | Ser | Arg |
| | | | | 325 | | | | | 330 | | | | | 335 | |
| Ile | Leu | Tyr | Pro | Asp | Glu | Val | Ala | Cys | Val | Ala | Pro | Glu | Val | Cys | Lys |
| | | | 340 | | | | | 345 | | | | | 350 | | |
| Arg | Val | Cys | Gly | Thr | Glu | Val | Gly | Cys | Ser | Asn | Ile | Ala | Tyr | Pro | Arg |
| | | 355 | | | | | 360 | | | | | 365 | | | |
| Leu | Val | Val | Lys | Leu | Met | Pro | Asn | Gly | Leu | Arg | Gly | Leu | Met | Leu | Ala |
| | 370 | | | | | 375 | | | | | 380 | | | | |
| Val | Met | Leu | Ala | Ala | Leu | Met | Ser | Ser | Leu | Ala | Ser | Ile | Phe | Asn | Ser |
| 385 | | | | | 390 | | | | | 395 | | | | | 400 |
| Ser | Ser | Thr | Leu | Phe | Thr | Met | Asp | Ile | Tyr | Thr | Leu | Arg | Pro | Arg | Ala |
| | | | | 405 | | | | | 410 | | | | | 415 | |
| Gly | Glu | Gly | Glu | Leu | Leu | Leu | Val | Gly | Arg | Leu | Trp | Val | Val | Phe | Ile |
| | | | 420 | | | | | 425 | | | | | 430 | | |
| Val | Ala | Val | Ser | Val | Ala | Trp | Leu | Pro | Val | Val | Gln | Ala | Ala | Gln | Gly |
| | | 435 | | | | | 440 | | | | | 445 | | | |
| Gly | Gln | Leu | Phe | Asp | Tyr | Ile | Gln | Ser | Val | Ser | Ser | Tyr | Leu | Ala | Pro |
| | 450 | | | | | 455 | | | | | 460 | | | | |
| Pro | Val | Ser | Ala | Val | Phe | Val | Val | Ala | Leu | Phe | Val | Pro | Arg | Val | Asn |
| 465 | | | | | 470 | | | | | 475 | | | | | 480 |
| Glu | Lys | Gly | Ala | Phe | Trp | Gly | Leu | Ile | Gly | Gly | Leu | Leu | Met | Gly | Leu |
| | | | | 485 | | | | | 490 | | | | | 495 | |
| Ala | Arg | Leu | Ile | Pro | Glu | Phe | Ser | Phe | Gly | Thr | Gly | Ser | Cys | Val | Arg |
| | | | 500 | | | | | 505 | | | | | 510 | | |
| Pro | Ser | Ala | Cys | Pro | Ala | Phe | Leu | Cys | Arg | Val | His | Tyr | Leu | Tyr | Phe |
| | | 515 | | | | | 520 | | | | | 525 | | | |
| Ala | Ile | Val | Leu | Phe | Phe | Cys | Ser | Gly | Leu | Leu | Ile | Ile | Ile | Val | Ser |
| | 530 | | | | | 535 | | | | | 540 | | | | |
| Leu | Cys | Thr | Ala | Pro | Ile | Pro | Arg | Lys | His | Leu | His | Arg | Leu | Val | Phe |
| 545 | | | | | 550 | | | | | 555 | | | | | 560 |
| Ser | Leu | Arg | His | Ser | Lys | Glu | Glu | Arg | Glu | Asp | Leu | Asp | Ala | Asp | Glu |
| | | | | 565 | | | | | 570 | | | | | 575 | |
| Leu | Glu | Ala | Pro | Ala | Ser | Pro | Val | Gln | Asn | Gly | Arg | Pro | Glu | His | |
| | | | 580 | | | | | 585 | | | | | 590 | | |
| Ala | Val | Glu | Met | Glu | Glu | Pro | Gln | Ala | Pro | Gly | Pro | Gly | Leu | Phe | Arg |
| | | 595 | | | | | 600 | | | | | 605 | | | |
| Gln | Cys | Leu | Leu | Trp | Phe | Cys | Gly | Met | Asn | Arg | Gly | Arg | Ala | Gly | Gly |
| | 610 | | | | | 615 | | | | | 620 | | | | |
| Pro | Ala | Pro | Pro | Thr | Gln | Glu | Glu | Glu | Ala | Ala | Ala | Ala | Arg | Arg | Leu |
| 625 | | | | | 630 | | | | | 635 | | | | | 640 |
| Glu | Asp | Ile | Asn | Glu | Asp | Pro | Arg | Trp | Ser | Arg | Val | Val | Asn | Leu | Asn |

-continued

```
                    645                              650                              655
Ala Leu Leu Met Met Ala Val Ala Met Phe Phe Trp Gly Phe Tyr Ala
            660                              665                              670
```

( 2 ) INFORMATION FOR SEQ ID NO:4:

( i ) SEQUENCE CHARACTERISTICS:
        ( A ) LENGTH: 662 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Oryctolagus cuniculus ( x i ) SEQUENCE DESCRIPTION: SEQ ID NO:4:

```
Met Asp Ser Ser Thr Leu Ser Pro Leu Thr Thr Ser Thr Ala Ala Pro
1               5                   10                  15
Leu Glu Ser Tyr Glu Arg Ile Arg Asn Ala Ala Asp Ile Ser Val Ile
                20                  25                  30
Val Ile Tyr Phe Leu Val Val Met Ala Val Gly Leu Trp Ala Met Phe
            35                  40                  45
Ser Thr Asn Arg Gly Thr Val Gly Gly Phe Phe Leu Ala Gly Arg Ser
    50                  55                  60
Met Val Trp Trp Pro Ile Gly Ala Ser Leu Phe Ala Ser Asn Ile Gly
65                  70                  75                  80
Ser Gly His Phe Val Gly Leu Ala Gly Thr Gly Ala Ala Ser Gly Ile
                85                  90                  95
Ala Thr Gly Gly Phe Glu Trp Asn Ala Leu Ile Met Val Val Val Leu
            100                 105                 110
Gly Trp Val Phe Val Pro Ile Tyr Ile Arg Ala Gly Val Val Thr Met
            115                 120                 125
Pro Glu Tyr Leu Gln Lys Arg Phe Gly Gly Lys Arg Ile Gln Ile Tyr
    130                 135                 140
Leu Ser Ile Leu Ser Leu Leu Leu Tyr Ile Phe Thr Lys Ile Ser Ala
145                 150                 155                 160
Asp Ile Phe Ser Gly Ala Ile Phe Ile Gln Leu Thr Leu Gly Leu Asp
                165                 170                 175
Ile Tyr Val Ala Ile Ile Ile Leu Leu Val Ile Thr Gly Leu Tyr Thr
            180                 185                 190
Ile Thr Gly Gly Leu Ala Ala Val Ile Tyr Thr Asp Thr Leu Gln Thr
            195                 200                 205
Ala Ile Met Met Val Gly Ser Val Ile Leu Thr Gly Phe Ala Phe His
    210                 215                 220
Glu Val Gly Gly Tyr Glu Ala Phe Thr Glu Lys Tyr Met Arg Ala Ile
225                 230                 235                 240
Pro Ser Gln Ile Ser Tyr Gly Asn Thr Ser Ile Pro Gln Lys Cys Tyr
                245                 250                 255
Thr Pro Arg Glu Asp Ala Phe His Ile Phe Arg Asp Ala Ile Thr Gly
            260                 265                 270
Asp Ile Pro Trp Pro Gly Leu Val Phe Gly Met Ser Ile Leu Thr Leu
            275                 280                 285
Trp Tyr Trp Cys Thr Asp Gln Val Ile Val Gln Arg Cys Leu Ser Ala
            290                 295                 300
Lys Asn Leu Ser His Val Lys Ala Gly Cys Ile Leu Cys Gly Tyr Leu
305                 310                 315                 320
```

-continued

| | | | | | | | | | | | | | | |
|---|---|---|---|---|---|---|---|---|---|---|---|---|---|---|
| Lys | Val | Met | Pro | Met 325 | Phe | Leu | Ile | Val | Met 330 | Met | Gly | Met | Val | Ser 335 | Arg |
| Ile | Leu | Tyr | Thr 340 | Asp | Lys | Val | Ala | Cys 345 | Val | Val | Pro | Ser | Glu 350 | Cys | Glu |
| Arg | Tyr | Cys 355 | Gly | Thr | Arg | Val | Gly 360 | Cys | Thr | Asn | Ile | Ala 365 | Phe | Pro | Thr |
| Leu | Val 370 | Val | Glu | Leu | Met | Pro 375 | Asn | Gly | Leu | Arg | Gly 380 | Leu | Met | Leu | Ser |
| Val 385 | Met | Met | Ala | Ser | Leu 390 | Met | Ser | Ser | Leu | Thr 395 | Ser | Ile | Phe | Asn | Ser 400 |
| Ala | Ser | Thr | Leu | Phe 405 | Thr | Met | Asp | Ile | Tyr 410 | Thr | Lys | Ile | Arg | Lys 415 | Lys |
| Ala | Ser | Glu | Lys 420 | Glu | Leu | Met | Ile | Ala 425 | Gly | Arg | Leu | Phe | Met 430 | Leu | Phe |
| Leu | Ile | Gly 435 | Ile | Ser | Ile | Ala | Trp 440 | Val | Pro | Ile | Val | Gln 445 | Ser | Ala | Gln |
| Ser | Gly 450 | Gln | Leu | Phe | Asp | Tyr 455 | Ile | Gln | Ser | Ile | Thr 460 | Ser | Tyr | Leu | Gly |
| Pro 465 | Pro | Ile | Ala | Ala | Val 470 | Phe | Leu | Leu | Ala | Ile 475 | Phe | Trp | Lys | Arg | Val 480 |
| Asn | Glu | Pro | Gly | Ala 485 | Phe | Trp | Gly | Leu | Val 490 | Leu | Gly | Phe | Leu | Ile 495 | Gly |
| Ile | Ser | Arg | Met 500 | Ile | Thr | Glu | Phe | Ala 505 | Tyr | Gly | Thr | Gly | Ser 510 | Cys | Met |
| Glu | Pro | Ser 515 | Asn | Cys | Pro | Thr | Ile 520 | Ile | Cys | Gly | Val | His 525 | Tyr | Leu | Tyr |
| Phe | Ala 530 | Ile | Ile | Leu | Phe | Val 535 | Ile | Ser | Ile | Ile | Thr 540 | Val | Val | Val | Val |
| Ser 545 | Leu | Phe | Thr | Lys | Pro 550 | Ile | Pro | Asp | Val | His 555 | Leu | Tyr | Arg | Leu | Cys 560 |
| Trp | Ser | Leu | Arg | Asn 565 | Ser | Lys | Glu | Glu | Arg 570 | Ile | Asp | Leu | Asp | Ala 575 | Gly |
| Glu | Glu | Asp | Ile 580 | Gln | Glu | Ala | Pro | Glu 585 | Glu | Ala | Thr | Asp | Thr 590 | Glu | Val |
| Pro | Lys | Lys 595 | Lys | Lys | Gly | Phe | Phe 600 | Arg | Arg | Ala | Tyr | Asp 605 | Leu | Phe | Cys |
| Gly | Leu | Asp 610 | Gln | Asp | Lys | Gly 615 | Pro | Lys | Met | Thr | Lys 620 | Glu | Glu | Glu | Ala |
| Ala | Met 625 | Lys | Leu | Lys | Leu | Thr 630 | Asp | Thr | Ser | Glu | His 635 | Pro | Leu | Trp | Arg 640 |
| Thr | Val | Val | Asn | Ile 645 | Asn | Gly | Val | Ile | Leu 650 | Leu | Ala | Val | Ala 655 | Val | Phe |
| Cys | Tyr | Ala | Tyr 660 | Phe | Ala | | | | | | | | | | |

NUCLEOSIDE COTRANSPORTER PROTEIN CDNA

GOVERNMENT RIGHTS

This invention was made with governmental support under National Institutes of Health grant number DK 19567. The government has certain rights in the invention.

FIELD OF THE INVENTION

The present invention relates to the identification and production of cotransporter membrane protein, and more particularly to the mammalian sodium dependent nucleoside cotransporter protein, to methods of using the cotransporter protein and to inhibitors of sodium dependent nucleoside transport into mammalian tissues.

BACKGROUND OF THE INVENTION

Cotransporter proteins are membrane-bound proteins that actively transport substances into cells. For example, organic substrates such as sugars, amino acids, carboxylic acids and neurotransmitters, are transported into eucaryotic cells by sodium ($Na^+$) cotransporter proteins. Some transport proteins have been identified, for example, $Na^+$/glucose and $Na^+$/proline transporters (Peerce and Wright, *Proc. Natl. Acad. Sci. USA* 8:2223-2226 (1984); Wright and Peerce, *J. Biol. Chem.* 259:14993-14996 (1984)), and the brain $Na^+$ \ $Cl^-$/GABA transporter (Radian et al., *J. Biol. Chem.* 261:15437-15441 (1986)), and progress has been made in locating their active sites and probing their conformational states (Peerce and Wright, supra; Wright and Peerce, supra; Peerce and Wright, *J. Biol. Chem.* 259:14105-14112 (1984); *J. Biol. Chem.* 260:6026-6031 (1985); *Proc. Natl. Acad. Sci. USA* 83:8092-8096 (1986); *Biochem.* 26:4272-4276 (1987)).

There appears to be a gene family of sodium ($Na+$) dependent transporters related to the mammalian intestinal $Na+$/glucose cotransporter, SGLT1. $Na+$/-glucose cotransporters have been cloned and sequenced from rabbit intestine (Hediger, et al, *Nature* 330:379-381 (1987)) and kidney (Coady, et al, *Am. J. Physiol.* 259:C605-C610 (1990)), human intestine (Hediger, et al, *Proc. Natl. Acad. Sci. USA* 86:5748-5752, and LLC-PK[1] cells (Ohta, et al, *Mol. Cell. Biol.* 10:6491-6499 (1990)). All of these transporters share greater than 80% identity of amino acid sequence. The only other proteins with significant homology to the mammalian SGLT1 are bacterial $Na+$-dependent transporters for proline (Nakao, et al, *Mol. Gen. Genet.* 208:70-75 (1987)) and pantothenate (Jackowski & Alix, *Bacteriol.* 172:3842-3848 (1990)). This suggests that the relationship between members of this multigene family is at the level of the transport mechanism, the $Na+$ coupling, rather than the substrate being transported.

Defects in $Na^+$-driven transporters may be associated with diseases. For example, a defect in the intestinal brush border $Na^+$/glucose cotransporter (SGLT1) is the origin of the congenital glucose-galactose malabsorption syndrome (Turk et al. *Nature* 350:354-356 (1991)).

It has been difficult to clone mammalian cotransport proteins in part because of the difficulties in purification of low abundance, hydrophobic membrane proteins that constitute less than 0.2% of the membrane protein. Hediger et al., *Nature* 330:379-381 (1987) described a new strategy for cloning rabbit intestinal $Na^+$/glucose cotransporter for expression without the use of antibodies or synthetic oligonucleotide probes.

Nucleosides direct a number of important physiological activities, particularly in the mammalian cardiovascular and central nervous systems. For example, adenosine is a potent vasoactive molecule in the coronary and cerebral vessels and a modulator of potassium and calcium channels in neurons and cardiac muscle (Belardinelli et al., *Prog. Cardiovasc. Diseases* 32:73-97 (1989)). Furthermore, nucleosides and their analogs are known to be potent cytotoxic and anti-retroviral agents. Nucleosides and their analogs, and nucleoside transport inhibitors are being used or proposed for use as broad spectrum anti-retroviral drugs, anti-cancer drugs, for treating ischemia and reperfusion-induced cell injury in the heart, and anti-arrhythmic drugs. For example, nucleoside transporter proteins may be useful to transport drugs to treat diseases such as AIDS (see, Yarchoan and Broder, *New Engl. J. Med.* 316:557-564 (1987)). In addition, membrane transport proteins are involved in the regulation of the uptake of nucleosides into cells. Nucleosides are required for normal growth, metabolism and function of cells. Some cells, such as bone marrow, leukocytes and brain cells, are deficient in purine biosynthesis and dependent on uptake of preformed purines.

Phloridzin, (1-[2-$\beta$-D-Glucopyranosyloxy)-4,6-dihydroxyphenyl]-3]-4-hydroxyphenyl)-1-propanone, No. 7300, p. 1163, Merck Index, 11th Edition, (1989)) a phloretin-2'-$\beta$-glucoside, is a natural substance occurring in all parts of the apple tree, and is known to be a very specific inhibitor of sugar transport in the mammalian intestine and kidney (see Newey et al., *J. Physiol.* 169:229-236 (1963) and Diedrich, *Methods in Enzymology* 191:755-780 (1990)). These effects are known to be due to competitive inhibition of active, i.e. sodium dependent, sugar transport. Fifty percent inhibition is achieved by phloridzin concentrations as low as $5\times10^{-6}$ molar. Phloridzin is very specific for the $Na^+$/glucose cotransporter protein because the glucose moiety is recognized by the active site on the membrane transport protein. There are no other known effects of phloridzin on biological. systems.

No other specific inhibitors of sodium dependent cotransporter proteins are known.

Nucleoside cotransporter proteins have been identified (Plageman et al., *Biochim. Biophys. Acta.* 947:405-554 (1988)), but have not been isolated, cloned and expressed. Therefore, these proteins are available in small quantities only from mammalian cell membranes. Thus, it would be desirable to have available a method for producing practical quantities of nucleoside cotransporter protein for use alone or with drugs that can be delivered into cells by the protein and to identify inhibitors that will specifically block the activity of the cotransporter protein.

SUMMARY OF THE INVENTION

The invention provides a means for obtaining mammalian nucleoside cotransporter protein in quantity.

Thus, in one aspect, the invention relates to recombinantly produced mammalian nucleoside cotransporter protein (SNST). This protein has an amino acid sequence substantially similar to that shown in FIG. 2 (SEQ ID NO:1). The invention further relates to a cDNA sequence and a genomic DNA sequence encoding mammalian SNST, to expression vectors suitable for production of this protein, to recombinant host cells transformed with these vectors, and to methods for producing recombinant SNST. In other aspects, the invention relates to the identification and use of inhibitors of the activity of SNST, and to compositions containing mammalian SNST or inhibitors of SNST, and to methods of using these compositions.

BRIEF DESCRIPTION OF THE DRAWINGS

FIG. 2 (SEQ ID NO:1) is the composite cDNA (bottom) sequence encoding mammalian SNST1 and the deduced amino acid (top) sequence of SNST1, obtained as described in Example 1, infra.

FIG. 3 is a comparison of the deduced amino acid sequences of SNST1 (top) and SGLT1 (bottom), obtained as described in Example 1, infra.

FIG. 4A and B are bar graphs representing the results of experiments demonstrating expression of chimeric SNST1 (SNST1c) in Xenopus oocytes as described in Example 1, infra (Abbreviations: U, uridine; 2-dU, 2-deoxyuridine; A, adenosine; C, cytidine; ddC, dideoxycytidine; G, guanosine).

DETAILED DESCRIPTION OF THE INVENTION

Figure 1:
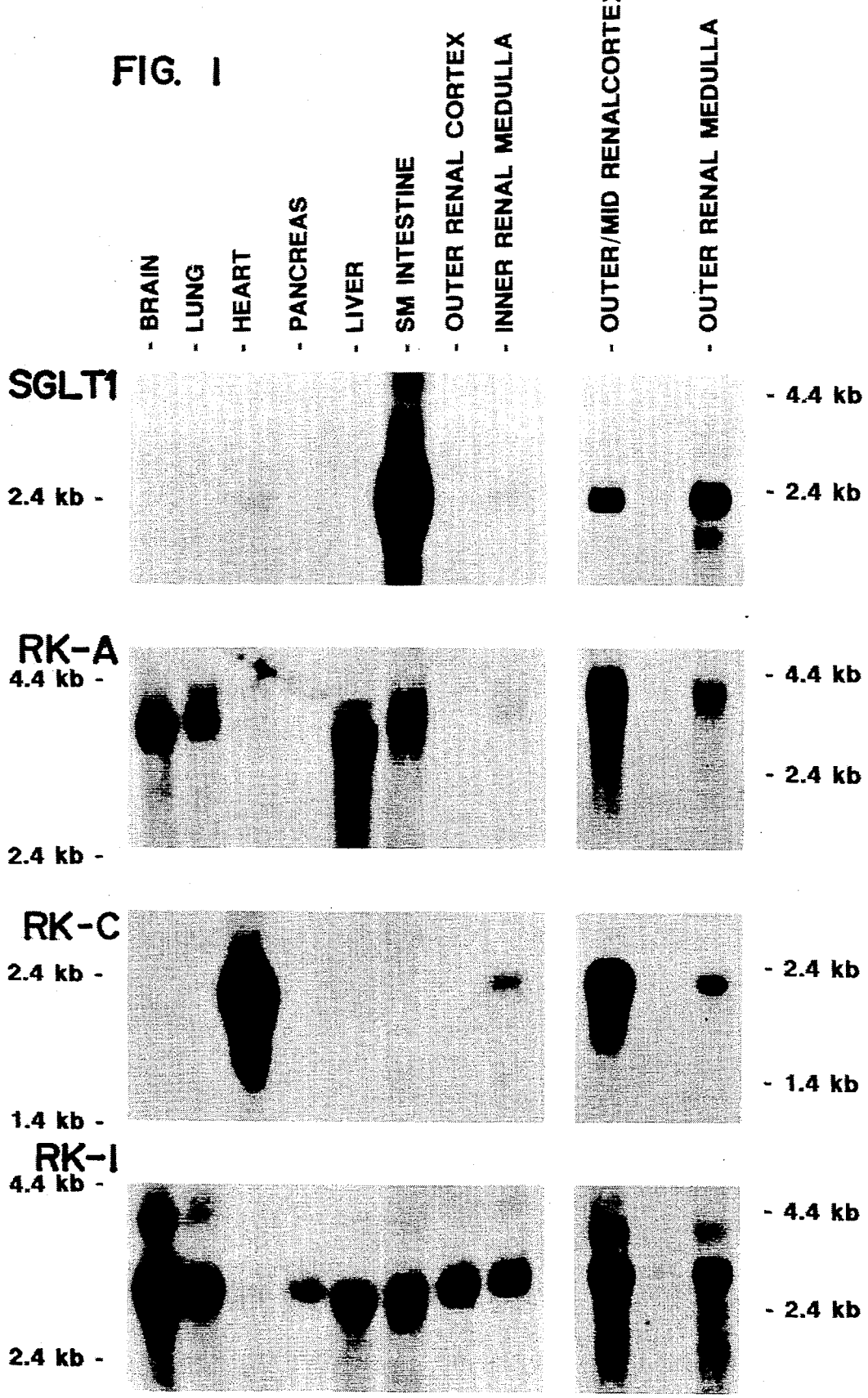
FIG. 1 is a photograph of a Northern blot showing the tissue distribution of rabbit intestinal Na+/glucose cotransporter (SGLT1) and SGLT1-related clones as described in Example 1, infra.

In order that the invention herein described may be more fully understood, the following description is set forth.

Definitions

As used herein, "Na+/nucleoside cotransporter protein (SNST or SNST1)" refers to the mammalian sodium nucleoside cotransporter membrane protein expressed from a clone obtained as described below. SNST1 has the amino acid sequence shown in FIG. 2. This protein has substantial homology with the amino acid sequence of mammalian intestinal Na+/glucose cotransporter (SGLT1). The mammalian SNST1 recombinant protein of this invention has an amino acid sequence substantially similar to that shown in FIG. 2, but minor modifications of this sequence which do not destroy activity also fall within the definition and within the protein of the invention. Also included within the definition are fragments of the entire sequence encoding SNST1 which retain activity.

As is the case for all proteins, SNST1 can occur in neutral form or in the form of basic or acid addition salts, depending on its mode of preparation, or, if in solution, upon its environment. In addition, the protein may be modified by combination with other biological materials such as lipids and saccharides, or by side chain modification, such as acetylation of amino groups, phosphorylation of hydroxyl side chains, or oxidation of sulfhydryl groups, or other modification of the encoded primary sequence. In its native form, SNST1 is probably a glycosylated protein and is associated with phospholipids. Included within the definition of SNST1 herein are glycosylated and unglycosylated forms, hydroxylated and nonhydroxylated forms, and any composition of an amino acid sequence substantially similar to that shown in FIG. 2 which retains the ability of the protein to transport nucleosides and nucleoside analogs across cell membranes.

It is further understood that minor modifications of primary amino acid sequence may result in proteins that have substantially equivalent or enhanced activity as compared to the sequence set forth in FIG. 2. These modifications may be deliberate, as by site-directed mutagenesis, or may be accidental, for example by mutation of hosts that are SNST1 producing organisms. All of these modification are included in the definition provided that activity of SNST1 is retained.

"SNST or SNST1 activity" is defined as sodium stimulated nucleoside uptake into cells. For example RNA encoding SNST1 is injected into Xenopus oocytes, and uptakes of labeled nucleosides as substrate, are measured after several days as a function of Na+ concentration. Transport is stopped by washing with choline solution containing excess unlabeled substrate. The oocytes are individually dissolved in SDS and assayed for radioactivity (see Coady et al., Arch. Biochem. Biophys. 283 (1):130–134 (1990)).

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host employed.

"Operably linked" refers to a positional arrangement wherein the components are configured so as to perform their usual function. Thus, control sequences operably linked to coding sequences are capable of effecting the expression of the coding sequence.

"Cells" or "recombinant host cells" or "host cells" are often used interchangeably herein as will be clear from the context. These terms include the immediate subject cell, and the progeny thereof. It is understood that not all progeny are exactly identical to the parental cell, due to chance mutations or differences in environment. However, such altered progeny are included when the above terms are used.

General Description

The methods illustrated below to obtain a cDNA sequence encoding mammalian SNST1, the gene for SNST and the SNST1 protein, are merely for purposes of illustration and are typical of those that might be used. However, other procedures may also be employed, as is understood in the art.

Cloning of Coding Sequences for Mammalian SNST1

The entire cDNA sequence encoding mammalian SNST1 protein has been cloned and expressed in Xenopus oocytes as set forth in Example 1, infra.

Complementary DNAs encoding seven different proteins related to the rabbit intestinal Na+/glucose cotransporter protein, SGLT1, designated RK-A-R-KI, were isolated from a rabbit renal cDNA library by high stringency hybridization with a fragment of the rabbit renal SGLT1 cDNA. One of the most abundant renal cDNAs, RK-C, was selected for more detailed characterization, and was found to encode most of SNST1

(nucleotides 66-2150). The composite sequence of SNST1 shown in FIG. 2 was obtained from two cDNAs, RK-C (nucleotides 66-2150) and RK-44 (nucleotides 20-2238, obtained by rescreening the library with RK-C) and by direct sequencing of rabbit renal mRNA. The full sequence of SNST1 (FIG. 2) encodes a protein of 672 amino acids. The sequence of SNST1 has significant homology with the amino acid sequence of rabbit intestinal SGLT1 (FIG. 3).

Expression of Mammalian SNST1

With the complete nucleotide sequence encoding mammalian SNST1 provided herein, the sequence may be expressed in a variety of systems. In Example 1, *infra*, the SNST1 RNA is used directly in a *Xenopus* oocyte expression system. To effect functional expression, a chimeric plasmid, SNST1c, was constructed because the SNST1 cDNAs lacked a start codon and poly(A+) tail. SNST1c RNA was then expressed in *Xenopus* ooyctes. Expression of SNST1c in *Xenopus* oocytes resulted in nucleoside-stimulated $^{22}$Na uptake and sodium-dependent $^{3}$H-uridine uptake. The uptake of H-uridine was inhibited by a range of nucleosides, including the anti-HIV drug, dideoxycytidine.

Standard Methods

The techniques for sequencing, cloning and expressing DNA sequences encoding the amino acid sequences corresponding to the Na+/nucleoside cotransporter protein, e.g PCR, synthesis of oligonucleotides, probing a cDNA library, transforming cells, constructing vectors, extracting messenger RNA, preparing cDNA libraries, and the like are well-established in the art, and most practitioners are familiar with the standard resource materials for specific conditions and procedures. However, the following paragraphs are provided for convenience and notation of modifications where necessary, and may serve as a guideline.

Sequencing:

Isolated cDNA and RNA encoding the SNST1 protein is analyzed by using a T7 sequencing kit (Pharmacia, Piscataway, N.J.) and synthetic oligonucleotides (Genosys Inc., San Diego, Calif.) as sequencing primers. Alternatively, cDNA is analyzed by restriction and/or sequenced by the dideoxy method of Sanger et al., *Proc. Nat. Acad. Sci. USA* 74:5463 (1977) as further described by Messing et al., *Nucleic Acids Res.* 9:309 (1981) or by the method of Maxam et al., *Methods in Enzymol.* 65:499 (1980).

Hosts and Control Sequences:

Both procaryotic and eucaryotic systems may be used to express the SNST1 protein; procaryotic hosts are the most convenient for cloning procedures. If procaryotic systems are used, an intronless coding sequence should be used, along with suitable control sequences. The cDNA of mammalian SNST1 can be excised using suitable restriction enzymes and ligated into procaryotic vectors along with suitable control sequences for such expression.

Procaryotes most frequently are represented by various strains of *E. coli*; however, other microbial strains may also be used. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* 198:1056 (1977)) and the tryptophan (trp) promoter system (Goeddel et al., *Nucleic Acids Res.* 8:4057 (1980)) and the lambda derived $P_L$ promoter and N-gene ribosome binding site (Shimatake et al., *Nature* 292:128 (1981)).

In addition to bacteria, eucaryotic microbes, such as yeast, may also be used as hosts. Laboratory strains of *Saccharomyces cerevisiae*, Baker's yeast, are most used although a number of other strains are commonly available. Vectors employing, for example, the 2 μ origin of replication of Broach, *Meth. Enz.* 101:307 (1983), or other yeast compatible origins of replications (see, for example, Stinchcomb et al., *Nature* 282:39 (1979)); Tschempe et al., *Gene* 10:157 (1980); and Clarke et al., *Meth. Enz.* 101:300 (1983)) may be used. Control sequences for yeast vectors include promoters for the synthesis of glycolytic enzymes (Hess et al., *J. Adv. Enzyme Reg.* 7:149 (1968); Holland et al., *Biochemistry* 17:4900 (1978)). Additional promoters known in the art include the promoter for 3-phosphoglycerate kinase (Hitzeman et al., *J. Biol. Chem.* 255:2073 (1980)), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. (See, for example, *Tissue Cultures*, Academic Press, Cruz and Patterson, Eds. (1973)). These systems have the additional advantage of the ability to splice out introns and thus can be used directly to express genomic fragments. Useful host cell lines include amphibian oocytes such as *Xenopus* oocytes, COS cells, VERO and HeLa cells, Chinese hamster ovary (CHO) cells and insect cells such as SF9 cells. Expression vectors for such cells ordinarily include promoters and control sequences compatible with mammalian cells such as, for example, the commonly used early and late promoters from baculovirus, vaccinia virus, Simian Virus 40 (SV 40) (Fiers, et al., *Nature* 273:113 (1973)), or other viral promoters such as those derived from polyoma, Adenovirus 2, bovine papilloma virus, or avian sarcoma viruses. The controllable promoter, hMTII (Karin, et al., *Nature* 299:797-802 (1982)) may also be used. General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in noncoding DNA regions. Origins of replication may be obtained, if needed, from viral sources. However, integration into the chromosome is a common mechanism for DNA replication in eucaryotes.

Transformations:

Depending on the host cell used, transformation is done using standard techniques appropriate to such cells. The treatment employing calcium chloride, as described by Cohen, *Proc. Natl. Acad. Sci. USA* (1972) 69:2110 (1972) or the CaCl$_2$ method described in Maniatis, et al., *Molecular Cloning: A Laboratory Manual*, Cold Spring Harbor Press, Sambrook et al., 2nd edition, (1989)) may be used for procaryotes or other cells which contain substantial cell wall barriers. For mammalian cells without such cell walls, the calcium phosphate precipitation method of Graham and van der Eb, *Virology* 52:546 (1978), optionally as modified by Wigler et al., *Cell* 16:777–785 (1979), may be used. Transformations into yeast may be carried out according to the method of Van Solingen et al., *J. Bact.* 130:946 (1977), or of Hsiao et al., *Proc. Natl. Acad. Sci. USA* 76:3829 (1979).

Other representative transfection methods include viral transfection, DEAE-dextran mediated transfection techniques, lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Cloning:

The cDNA sequences encoding SNST1 were obtained from screening of a rabbit kidney cDNA library using high stringency hybridization with rabbit renal SGLT1 cDNA.

Alternatively, the cDNA sequences encoding SNST1 are obtained from a cDNA library prepared from mRNA isolated from cells expressing SNST1 according to procedures described in *Molecular Cloning: A Laboratory Manual*, Cold Spring Harbor, second edition, Sambrook et al. (1989), with particular reference to Young et al., *Nature*, 316:450–452 (1988). The cDNA insert from the successful clone, excised with a restriction enzyme such as EcoRI, is then used as a probe of the original cDNA library to obtain the additional clones containing inserts encoding other regions of SNST1, that, together with this probe, span the nucleotides containing the complete coding sequence of SNST1.

Probing cDNA:

A cDNA library is screened using high stringency conditions as described by Ausubel et al., in *Current Protocols in Molecular Biology*, Greene Publishing and Wiley-Interscience, New York. (1990) or using methods described in *Molecular Cloning: A Laboratory Manual*, Cold Spring Harbor, Sambrook et al., eds., second edition (1989), with particular reference to Young et al., *Nature*, 316:450–452 (1988), or using the colony hybridization procedure with a fragment of the rabbit renal SGLT1.

cDNA Library Production:

Double-stranded cDNA is synthesized and prepared for insertion into a plasmid vector such as Bluescript ® or Lambda ZAP ® (Stratagene, San Diego, Calif.) using standard procedures (see *Molecular Cloning: A Laboratory Manual*, Cold Spring Harbor, Sambrook et al., eds. second edition (1989).

Vector Construction:

Construction of a suitable vector containing the desired coding and control sequences employs standard ligation and restriction techniques which are well understood in the art. (Young et al., *Nature* 316:450–452 (1988)).

Site specific DNA cleavage is performed by treating with the suitable restriction enzyme, such as EcoRI, (or enzymes) under conditions which are generally understood in the art, and the particulars of which are specified by the manufacturer of these commercially available restriction enzymes. See, e.g., New England Biolabs, Product Catalog. In general, about 1 $\mu$g of phage DNA sequence is cleaved by one unit of enzyme in about 20 $\mu$l of buffer solution; in the examples herein, typically, an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, and may be followed by ether extraction and the nucleic acid recovered from aqueous fractions by precipitation with ethanol.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na+ and Mg+$^2$ using about 1 unit of BAP or CIP per $\mu$g of vector at 60° C. or 37° C., respectively, for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Ligations are performed in 15–50 $\mu$l volumes under the following standard conditions and temperatures: 20 mM Tris-Cl, pH 7.5, 10 mM MgCl$_2$, 10 mM DTT, 33 $\mu$g/ml BSA, 10 mM–50 mM NaCl, and either 40 $\mu$M ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 $\mu$g/ml total DNA concentrations (5–100 nM total end concentration). Intermolecular blunt end ligations (usually employing a 10–30 fold molar excess of linkers) are performed at 1 $\mu$M total ends concentration.

Verification of Construction:

Correct ligations for vector construction are confirmed according to the procedures of Young et al., *Nature*, 316:450–452 (1988).

Isolation of Gene Encoding SNST1:

The cDNA of SNST1 obtained as described above is then used as a probe of a genomic mammalian cDNA library to obtain clones containing the complete gene coding sequence of mammalian SNST1. Alternatively, sets of synthetic oligonucleotides encoding SNST1 are used to probe a genomic cDNA library. Successful hybridizing clones are sequenced, and those containing the correct N-terminal sequence for SNST1 are obtained.

Expression:

The SNST1 protein may be expressed in a variety of systems as set forth below. The cDNA may be excised by suitable restriction enzymes and ligated into procaryotic or eucaryotic expression vectors for such expression.

Protein Recovery:

SNST1 protein may be produced either as a mature protein or as a fusion protein, or may be produced along with a signal sequence in cells capable of processing this sequence for secretion. It may be advantageous to obtain secretion of the protein as this minimizes the difficulties in purification. Cultured mammalian cells are able to cleave and process heterologous mammalian proteins containing signal sequences and to secrete them into the medium (McCormick et al., *Mol. Cell. Biol.* 4:166 (1984)).

The protein is recovered using standard protein purification techniques including immunoaffinity purification. If secreted, the purification process is simplified, because relatively few proteins are secreted into the medium, and the majority of the secreted protein will, therefore already be SNST1. However, it is also known in the art to purify the protein from membranes of cells in which it is produced in mature or fully processed form.

USE

SNST1 protein, when expressed in functional form in a host cells such as a *Xenopus* oocyte, can be used to screen compounds, e.g. nucleoside analogs and other drugs to identify those capable of more effective uptake into appropriate cells.

SNST1 may also be used to screen compounds for inhibition of sodium dependent nucleoside transport. Such inhibitors include phloridzin, described above, and phloridzin analogs. Phloridzin analogs may be isolated from natural sources (Newey et al., *supra*) or are synthesized by standard chemical procedures (Diedrich, *supra*). For example, different phloretin sugar glycosides are made by mixing phloretin and acetobromo-D-sugars (e.g. ribose) in cold 0.25N KOH, incubating in the deoxygenated solution in the dark for 24 hours and then adding acetic acid. The sticky solid product is collected, washed, dried and extracted with $CHCl_3$. The tetraacetylglucosides are then separated using conventional chromatography, and saponified in cold methanolic sodium methoxide. Different phloretin analogs are prepared as described by Diedrich, (1990) *supra;* Diedrich, *Biochim. Biophys. Acta.* 71:688–700 (1968); Diedrich, *Arch. Biochem. Biophys.* 117:248–256 (1966) and Lin et al., *Biochim. Biophys. Acta* 693:379–388 (1982)).

In addition, inhibitors of nucleoside transport, consisting of phloridzin, phloridzin analogs, nucleoside analogs and other reagents, may be designed using the nucleoside transport assay described herein and the $Na^+$/nucleoside cotransporter protein of the invention to identify effective inhibitor compounds.

In addition, SNST1 protein may be used to prepare antibodies, including polyclonal and monoclonal antibodies that bind to the SNST1 protein. These antibodies may be used to purify SNST1 protein. They may also be screened using the nucleoside transport assay described herein to identify those capable of inhibiting nucleoside transport by SNST1.

Monoclonal antibodies reactive with SNST1, may be produced by hybridomas prepared using known procedures, such as those introduced by Kohler and Milstein (see Kohler and Milstein, *Nature,* 256:495–97 (1975)), and modifications thereof, to regulate cellular interactions.

These techniques involve the use of an animal which is primed to produce a particular antibody. The animal can be primed by injection of an immunogen (e.g. the SNST1 protein or fusion proteins) to elicit the desired immune response, i.e. production of antibodies from the primed animal. A primed animal is also one which is expressing a disease. Lymphocytes derived from the lymph nodes, spleens or peripheral blood of primed, diseased animals can be used to search for a particular antibody. The lymphocyte chromosomes encoding desired immunoglobulins are immortalized by fusing the lymphocytes with myeloma cells, generally in the presence of a fusing agent such as polyethylene glycol (PEG). Any of a number of myeloma cell lines may be used as a fusion. partner according to standard techniques; for example, the P3-NS1/1-Ag4-1, P3-x63-Ag8.653, Sp2/0-Ag14, or HL1-653 myeloma lines. These myeloma lines are available from the ATCC, Rockville, Md.

The resulting cells, which include the desired hybridomas, are then grown in a selective medium such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of the desired specificity, e.g. by immunoassay techniques using the SNST1 protein that has been used for immunization. Positive clones can then be subcloned under limiting dilution conditions, and the monoclonal antibody produced can be isolated.

Various conventional methods can be used for isolation and purification of the monoclonal antibodies so as to obtain them free from other proteins and contaminants. Commonly used methods for purifying monoclonal antibodies include ammonium sulfate precipitation, ion exchange chromatography, and affinity chromatography (see Zola et al., in *Monoclonal Hybridoma Antibodies: Techniques and Applications,* Hurell (ed.) pp. 51–52 (CRC Press, 1982)). Hybridomas produced according to these methods can be propagated *in vitro* or *in vivo* (in ascites fluid) using techniques known in the art (see generally Fink et al., *Prog, Clin. Pathol.,* 9:121–33 (1984), FIG. 6-1 at p. 123).

Generally, the individual cell line may be propagated *in vitro*, for example, in laboratory culture vessels, and the culture medium containing high concentrations of a single specific monoclonal antibody can be harvested by decantation, filtration, or centrifugation.

In addition, fragments of these antibodies. containing the active binding region reactive with the SNST1 protein, such as Fab, $F(ab')_2$ and Fv fragments may be produced. Such fragments can be produced using techniques well established in the art (see e.g. Rousseaux et al., in *Methods Enzymol.,* 121:663–69, Academic Press (1986)).

Polyclonal antibodies may be produced, for example polyclonal peptide antibodies as described by Hirayama et al., in *Am. J. Physiol.* 261:C296–C304 (1991). Briefly, peptides are synthesized, e.g. as described by Kent and Clark-Lewis, in Synthetic Peptides in Biology and Medicine, Amsterdam, Elsevier, p. 29–57 (1985), and are purified using reverse-phase high-performance liquid chromatography on a preparative $C_8$ column in a gradient of 17.5–32.5% acetonitrile with 0.1% trifluoroacetic acid (TFA). The purity of the product is verified by isocratic elution on a $C_{18}$ column in 25.5% acetonitrile and 0.1% TFA and by mass spectroscopy before lyophilization. Polyclonal antibodies are then raised in rabbits following standard procedures using the peptides as immunogen. These procedures permit the production of antibodies that bind to defined regions of the SNST1 amino acid sequence, using peptides or portions of peptides of the SNST1 protein as immunogen.

The following examples are presented to illustrate the present invention and to assist one of ordinary skill in the art in making and using the invention. The examples are not intended in any way to otherwise limit the scope of the invention.

EXAMPLE 1

Cloning and Expression of Mammalian Na+/Nucleoside Cotransporter Protein

This example describes the cloning and expression of a mammalian Na+/nucleoside cotransporter protein.

A rabbit renal cDNA library was screened for clones related to the Na+/glucose cotransporter protein, SGLT1, because the kidney contains a number of Na+-dependent cotransporters.

cDNA Library screening. A rabbit kidney cDNA library in Lambda ZAP ®, provided by Drs. Philpot and Ryan (National Institute of Environmental Health Sciences (NIEHS), Triangle Park, N.C.) was screened under high stringency conditions (hybridization at 42° C. in 50% formamide and washing at 50° C. in 0.1XSSC, as described by Ausubel et al. (eds.), in Current Protocols in Molecular Biology, Greene Publishing and Wiley-Interscience, New York (1990), incorporated by reference herein, with a $^{32}$p-labeled 1.6 kb HindIII/XhoI fragment of the rabbit renal Na+/glucose cotransporter (Coady et al., *Am. J. Physiol.* 259:C605-C610 (1990)). pBluescript SK ® (Stratagene), containing cDNA for SNST1, was excised from positive phage following the manufacturer's directions. All subsequent experiments were conducted using the plasmids. The rabbit kidney library was also screened with RK-C, one of the cDNAs isolated during the first round.

RNA Preparation and Northern Blots. Poly(A+) RNA preparation and Northern transfers were as follows. The samples used for preparation of RNA were immediately frozen in liquid nitrogen and then stored until use, up to one week at −80° C. The RNA was prepared by CsCl centrifugation (Ausubel et al., *supra,* incorporated by reference herein) using a modified homogenization buffer (Chomczynski and Sachhi, *Anal. Biochem.* 162:156-159 (1987), incorporated by reference herein). Poly(A+)RNA was selected by oligo(dT) chromatography (Jacobson, *Meths. Enzymol.* 152:254-261 (1987), incorporated by reference herein) but LiCl replaced NaCl in all solutions. Before the final precipitation, the mRNA was centrifuged through a Costar 0.45 μm filter to remove any particulates from the oligo(dT) column that would otherwise clog an oocyte injection needle. RNA samples were stored at −80° C.

Two Northern blots containing mRNA from a range of rabbit tissues and rabbit kidney were probed in turn with cDNAs for SGLT1 and SGLT1-related clones. Whole organs were used except for the intestine and kidney samples. The intestinal RNA was prepared from jejunal mucosal scrapings. The outer cortex sample represents the outer 1 mm of renal cortex, and inner renal medulla represents papilla. The outer/mid-cortex sample contained approximately the outer 2 mm of kidney, and the outer medulla sample was prepared from outer strips of medulla. The RNA from each sample was separated in a 1% agarose gel containing 0.66M formaldehyde (Davis et al., in Basic Methods in Molecular Biology,. New York, Elsevier Science (1986), incorporated by reference herein), transferred to reinforced nitrocellulose filters (Duralose ®, Stratagene) and fixed to the filters by ultraviolet crosslinking (Stratalinker ®, Stratagene). Filters were prehybridized at least six hours at 42° C. in 50% formamide, 5XSSC (Davis et al, *supra*), 3X Denhart's (Davis et al., *supra*), 25 mM sodium phosphate buffer (pH 6.5), 0.2% sodium dodecyl sulfate (SDS), 10% Dextran sulfate, and 250 μg/ml Prehybe-HS (Lofstrand Labs, Gaithersburg, Md.). Gel-purified cDNA excised with EcoRI consisting of the coding region of the rabbit intestinal Na+/glucose cotransporter (Coady et al., *Am. J. Physiol.* 259:C605-C610 (1990)) was labelled with $^{32}$P-dCTP using an Oligolabelling kit (Pharmacia) and used as the probe. The blots were hybridized at 42° C. overnight. Washes were as follows: 15 min at room temperature in 5XSSC; 0.1% SDS; 0.05% sarkosyl; 15 min at 60° C. in 5XSSC, 0.1% SDS, 0.05% sarkosyl; three 15 min washes at 60° C. in 0.1XSSC, 0.1% SDS (Coady et al., *supra*). Each lane contained 5 μg of mRNA. Size standards are indicated in FIG. 1. Autoradiography was carried out at −80° C. and autoradiograms were scanned with a Hoefer GS300 (San Francisco, Calif.) densitometer.

cDNA and RNA sequencing. Double-stranded sequencing of both strands of cDNA was carried out using a T7 sequencing kit (Pharmacia) and synthetic oligonucleotides (Genosys Inc., San Diego, Calif.) as sequencing primers. Deaza nucleotide mixes were used when necessary to resolve compressions. Nucleotides 1-80 of SNST1 were directly sequenced from renal RNA according to Geliebter, *Focus* 9:5-8 (1989), incorporated by reference herein, with a reaction temperature of 50° C., avian myeloblastosis virus (AMV) reverse transcriptase (Life Sciences, Bethesda, Md.) and gel-purified primers and end-labelled with $^{32}$p.

Construction of chimera pSNST1c. In order to determine the function of SNST1, a cDNA chimera, SNST1c, was constructed for functional expression of SNST1. SNST1c provided the missing start codon and poly(A+) tail of the SNST1 cDNAs (RK-C and RK44). SNST1c consisted of nucleotides 243-2150 of SNST1 (amino acids 80-672) together with the 5' end (5' untranslated region and amino acids 1-79) and the 3' untranslated region of the rabbit SGLT1. The 5' end of pRK-C (to nucleotide 178, MscI site) was replaced by nucleotides 1-268 (also at an MscI site) of the rabbit intestinal SGLT1, pMC424 (Hediger et al., *Nature* 330:379-381 (1987)). The 3' end of pMC424 was cut at the XhoI site and nucleotides 2014-2225, containing the entire 3' untranslated region and poly(A+) tail, were attached to the end of the 3'UTR of pRKC. This construct was difficult to grow in pBluescript ™ and was subcloned into the HindIII/KpnI sites of pT7/T3-18 (BRL Laboratories, Bethesda, Md.), which lacked the lacZ gene.

Expression of pSNST1c. The chimeric plasmid pSNST1c was linearized using KpnI and RNA was synthesized *in vitro* with an RNA transcription kit (Stratagene). The function of SNST1c was determined by expression of RNA in *Xenopus* oocytes as described below.

Oocyte injections. *Xenopus* oocytes were dissected and injected, and transport was measured as described below. Stage V and VI oocytes (Dumont, *J. Morphol.* 136:153-180 (1972)) from *Xenopus laevis* (Xenopus One, Ann Arbor, Mich.) were dissected and defolliculated as described by Hediger et al., *Proc. Natl. Acad. Sci. USA* 84:2634-2637 (1987) and Coady et al., *Arch. Biochem. Biophys.* 265:73-81 (1990), both of which are incorporated by reference herein. Briefly, oocytes were hand-dissected from ovarian tissue of adult female *Xenopus laevis.* Individual oocytes were obtained by gentle agitation in Barth's solution (Silbernagl, *Physiol. Rev.* 68:912-1007 (1988)) 1.0% collagenase (to remove follicular cells) and 0.1% trypsin inhibitor for 60 min followed by a 30 to 60 min incubation in 100 mM $K_2HPO_4$, pH 6.5, 0.1% BSA (modified from Dumont, J. Morphol. 136:153-179 (1972)). Oocytes were maintained in Barth's solution at 18° C. After 16 to 24 hr, the healthy oocytes were injected with 50 nl of water or mRNA (0.2 to 1 mg/ml) and incubated in Barth's solution with gentamicin at 18° C. for another 3 to 8 days.

Assay of Transporter Activity $Na^+$/nucleoside transporter activity was assayed by measuring the $Na^+$-dependent uptake by the chimeric construct, SNST1c. Initial screening of SNST1c function utilized radiolabelled substrates, including sugars (α-methyl-D-glucopyranose [αMDG],D-glucose, 3-O-methylglucose), L-amino acids (alanine, glutamate, lysine, methyl-aminoisobutyric acid, phenylalanine, proline, taurine), carboxylic acids (succinate, lactate) and vitamins (biotin, pantothenate), but none of these was transported. Because of the sequence similarity to SGLT1, it was hypothesized that the transport would be $Na^+$-dependent. Therefore, the uptake of $^{22}Na^+$ in the presence of potential substrates was monitored.

Measurements were made of [$^3H$] uridine uptake in oocytes expressing SNST1c (FIG. 4A and 4B). Uptakes were measured over 5 min in a buffer containing either 100 mM NaCl, choline chloride or LiCl as described by Coady et al., Arch. Biochem. Biophys. 283:130-134 (1990), incorporated by reference herein. [All of the solutions contained 2 mM KCL, 1 mM $MgCl_2$, 1 mM $CaCl_2$, 10 mM HEPES/Tris, pH 7.5 and either 100 mM NaCl ($Na^+$ transport buffer) or 100 mM choline-Cl (choline transport buffer). The uptake solutions contained radiolabeled substrate while the wash solutions contained nonradioactive substrate. Oocytes were injected with water as a control, or SNST1c cRNA (50 ng). Oocytes were preincubated for 30 min in substrate-free choline transport buffer when uptakes in $Na^+$ and choline were to be compared. Transport of substrate was assayed by placing 4-6 oocytes in 0.5 ml of radioactive uptake solution, preceded by a 30 min preincubation in a $Na^+$-free (100 mM choline-Cl) solution when $Na^+$-dependent transport was to be measured. Transport was stopped by washing the oocytes five times with 4 ml of ice-cold choline solution containing excess unlabeled substrate. The oocytes were individually dissolved in 1.0 ml of 10% SDS and assayed for radioactivity. All data are expressed as mean ±SD. FIG. 4A indicates cation dependence of 1 μM [$^3H$]uridine uptake in oocytes expressing SNST1c 4 days post-injection. In addition, inhibition of 0.6 μM [$^3H$]uridine uptake in oocytes by 1 mM nucleosides was determined (FIG. 4B). Uptakes were measured in $Na^+$ containing buffer (Coady et al., supra) Oocytes were injected with water as a control, or SNST1c cRNA (50 ng).

Results

Seven distinct cDNAs, RK-A through RK-I, were isolated from the rabbit kidney library by high stringency hybridization with the rabbit renal SGLT1 cDNA as described above. The renal cDNAs were different from one another as shown by partial restriction mapping and DNA slot blot hybridization. The tissue distribution of mRNA encoding SGLT1 and the SGLT1-related clones is shown in FIG. 1. Rabbit tissues are shown on the left, and rabbit kidney is shown on the right. Panels from top to bottom were probed with SGLT1, RK-A, RK-C (nucleotides 66-2150 of SNST1) and RK-I.

As has been observed previously, the rabbit SGLT1 mRNA was predominantly a single species of 2.3 kb found in intestine and kidney (Hediger et al., Nature 330:379-381 (1987); and Coady et al., Am. J. Physiol. 259:C605-C610 (1990)). The signal was stronger in outer renal medulla than cortex. No other tissue tested gave a signal with SGLT1. The message size of RK-A was approximately 4 kb and was distributed predominantly in brain, lung, liver, intestine and also kidney. There was a single mRNA species for RK-C at approximately 2.3 kb, which was more abundant in heart than in kidney. RK-C appeared to be absent from the outer cortex but present in other parts of the kidney. Four other renal cDNAs (RK-B, RK-D, RK-E, RK-F) had similar tissue distributions as RK-C mRNA, although the message size for RK-D was smaller, about 2.2 kb. Finally, RK-I mRNA was approximately 3 kb and was found in all tissues tested: brain, lung, heart, pancreas, liver, intestine, kidney.

One of the renal cDNAs, RK-C, was selected for more detailed characterization and, based on results of expression studies, this clone encoded most of the SNST1 protein. The composite sequence of SNST1 is shown in FIG. 2. The sequence was obtained from two cDNAs: RK-C (nucleotides 66-2150) and RK-44 (nucleotides 20-2238, obtained by rescreening the library with RK-C), and by direct sequencing of rabbit renal mRNA (nucleotides 1-80). All overlapping sequences were identical. The two cDNAs contain an ATG (nucleotides 136-138) which was initially considered as a putative start codon. In vitro translation experiments showed that RK-C and the rabbit intestinal SGLT1 both made proteins of 47 kDa (in 8% acrylamide), which increased by 6 kDa to 53 kDa in the presence of pancreatic microsomes. The putative start codon was rejected for three reasons: (1) there was high identity between the sequence upstream of this ATG and the coding region of SGLT1 (FIG. 3); 2) the equivalent ATG was not used for initiation of translation in SGLT1, as there was no functional expression of a 5'-truncated SGLT1, although protein was detected in in vitro translation experiments; and (3) the sequences flanking the ATG at nucleotides 136-138 do not form a consensus initiation sequence (Kozak, Microbiol. Revs., 47:1-45 (1983)).

The full sequence of SNST1 (FIG. 2) contains a single open reading frame which encodes a protein of 672 amino acids. The 5' untranslated region is approximately 30 nucleotides long and there is a consensus initiation. sequence, YNNAUGG (Kozak, M., Microbiological reviews, 47:1-45 (1983)). The 3' untranslated region contains a consensus polyadenylation sequence, AAUAAA, (underlined in FIG. 2) but there is no poly(A+) tail.

Figure 5:
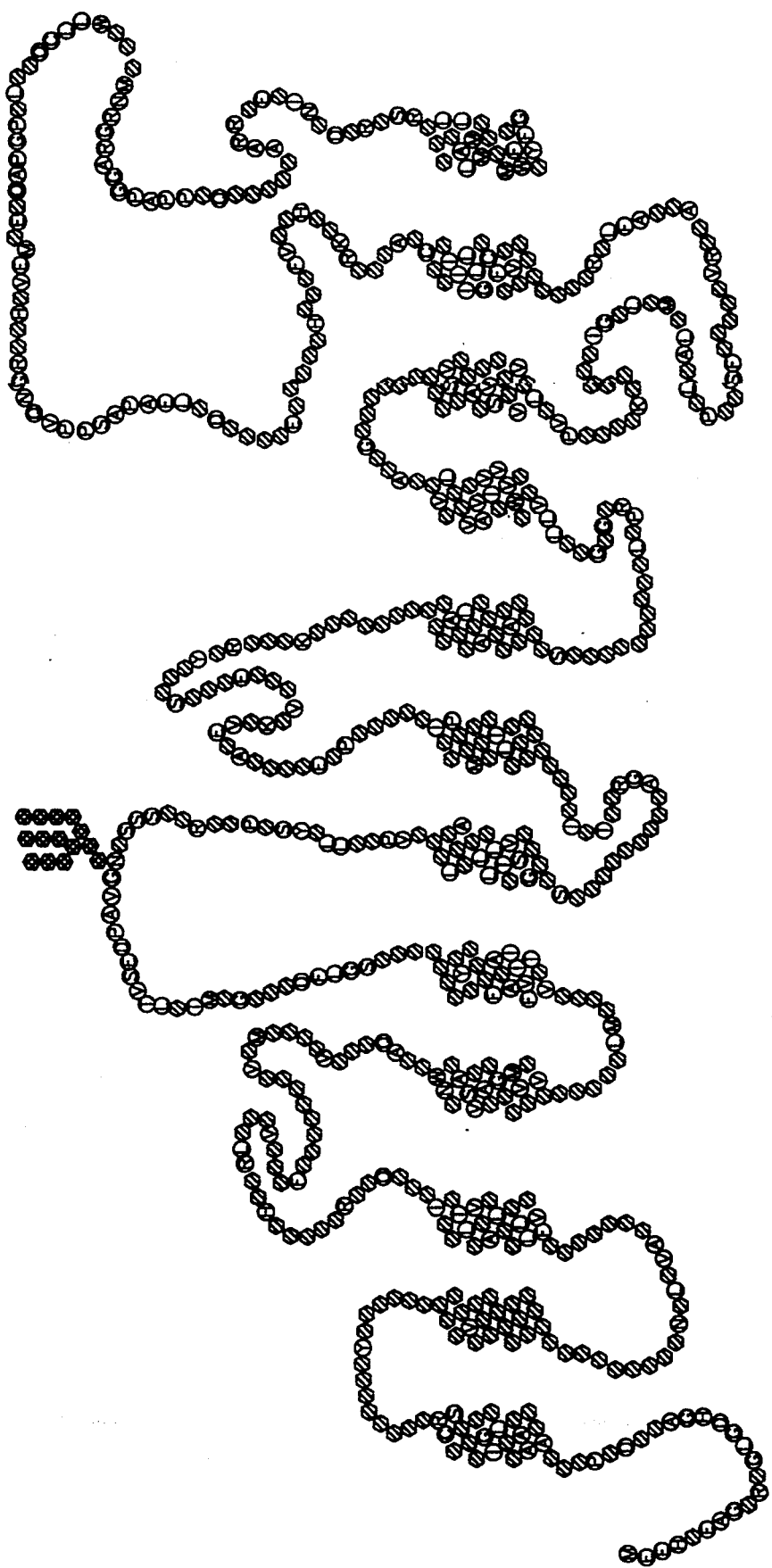
FIG. 5 is a depiction of the predicted secondary structure model of SNST1 obtained as described in Example 1, infra (residues identical with SGLT1 are filled in).

The sequence similarity between SNST1 and the rabbit SGLT1 is shown in FIGS. 3 and 5 (SNST1-top; SGLT1-bottom). The alignment was made using the widely available Genetics Computer Group program, GAP (Devereux et al., Nucleic Acids Res. 12:387-395 (1984). Lines in FIG. 3 denote identical amino acids, and colons show chemically similar amino acids. The hybrid transporter, SNST1c, used for expression experiments, contained amino acids 1-79 of SGLT1 attached to amino acids 80-872 of SNST1. The three predicted N-glycosylation sites (at $N^{250}$, $N^{306}$, $N^{399}$), conserved residues $D^{25}$, $G^{40}$, $R^{300}$, "SOB motif" (-GLY - - - ALA- X-X-X-X-LEU-X-X-X-GLY-ARG-) described by Deguchi et al., *J. Biol. Chem.* 265:21704–21708 (1990), and $G^{380}$, $A^{416}$, $L^{421}$, $G^{425}$, $R^{426}$, are indicated.

There is 61% identity and 80% similarity between the two sequences, including regions of striking identity, particularly toward the amino-terminus. SNST1 contains three putative N-linked glycosylation sites, two of which are shared with SGLT1 and a third that may be in a transmembrane helix. A single residue, $Asn^{248}$, is N-glycosylated in SGLT1 (Hediger, et al, *Biophys. Biochim. Acta,* 1064:360–364 (1991) and this may be the case for SNST1 as the extent of glycosylation seen after *in vitro* translation (increase of 6 kDa in the presence of microsomes) appears to be the same for both transporters. The hydropathy plots of SNST1 and SGLT1 are also very similar, and a model of the predicted secondary structure of SNST1, a membrane protein with 12 transmembrane domains, is shown in FIG. 5. The predicted structure was based on Kyte-Doolittle analysis (Kyte and Doolittle, *J. Mol. Biol.* 147:105 (1982)). Intracellular residues are shown in FIG. 5 below, and extracellular residues are shown above the putative transmembrane helices. Residues identical with SGLT1 are filled circles in the figure. SNST1 is ten amino acids longer than SGLT1 and most of the additional amino acids have been inserted into the large extracellular loop between transmembrane helices 11 and 12.

SNST1 is intermediate in sequence homology between the mammalian SGLT1-type Na+/glucose cotransporters, which share more than 80% of their residues, and the bacterial Na+/proline (PutP) (Nakao et al, *Mol. Gen. Genet,* 208:70–75, (1987)) and Na+/pantothenate (PanF) transporters (Jackowski and Alix, *Bacteriol,* 172:3842–3848, (1990), which have about 25% identity with the SGLT1s. Many of the residues conserved between the mammalian SGLT1s and bacterial PutP and PanF are also conserved in SNST1. These include $Gly^{43}$ and $Arg^{300}$, which are implicated in Na+ binding (Yamato et al, *J. Biol. Chem.,* 265:2450–2455, (1990)), and the SOB motif (Deguchi et al., *supra*) (FIG. 2). Finally, $Asp^{28}$, the residue that is mutated to asparagine in the SGLT1 of patients with glucose-galactose malabsorption syndrome (Turke et al., *Nature* 350:354–356 (1990), is conserved in SNST1 at position 25.

The sequences of SNST1 and SGLT1 show remarkable similarity at their 5' ends (FIG. 3), so that only portions of the N-terminus and first transmembrane helix of SNST1 were changed (the new segment contained 51 identical and 11 conserved amino acids out of a total of 79). This approach may prove useful to those wishing to express a 5'-untruncated cDNA or to increase the expression of a poorly-expressing cDNA.

A positive signal was observed with a pool of nucleosides (adenosine, uridine, guanosine, and cytidine) but no signals were seen with other substrates ($\alpha$-MDG, myoinositol, betaine, thiamine, cholate pyruvate). In the presence of nucleosides, water-injected oocytes transported 297±99 pmol $^{22}$Na+/oocyte/hr while SNST1c-injected oocytes transported 752±162 pmol $^{22}$Na/oocyte/hr (n=8 oocytes). Control experiments showed that the Na+/glucose cotransporter did not transport nucleosides (water-injected:248±56, SGLT1-injected 309±78, SNST1c-injected=722±108 fmol $^3$H-uridine/oocyte/hr, n=5 oocytes) and, conversely, oocytes injected with SNST1c RNA do not transport sugars (water:0.4±0.1, SGLT1:70±19, SGLT1c:0.5±0.1 pmol $^{14}$C-$\alpha$MDG/oocyte/hr, n=6 oocytes). This suggests that the first 79 amino acids of these transporters do not determine sugar or nucleoside specificity.

Oocytes injected with SNST1c RNA transported [$^3$H]-uridine in the presence of Na+, and transport was inhibited when Na+ was replaced by choline or Li+ (FIG. 4A). There also appeared to be Na+/nucleoside cotransport in the oocyte membrane, and this transport differed from SNST1c in substrate specificity (e.g., dideoxycytidine did not inhibit the oocyte transporter but did inhibit SNST1c). The transport of uridine by SNST1c was inhibited by a variety of nucleosides including uridine, 2-deoxyuridine, adenosine, guanosine and cytidine, as well as dideoxycytidine, a drug currently in clinical trials for use in AIDS therapy (FIG. 4B). This broad substrate specificity is characteristic of Na+/uridine cotransport in brush border membranes from rat (Lee et al., *Am. J. Physiol.* 258:F1203–F1210 (1990)) and rabbit (Williams et al., *Biochem.* 284:223–231 (1989) kidney.

Although not being bound by any particular theory of the mechanism of action of SNST1, the physiological function of SNST1 in the kidney may be in the reabsorption of nucleosides from the glomerular filtrate by the proximal tubule, as Na+-dependent nucleoside transport has been reported for the cortical brush border, but not basolateral, membrane (Williams et al., *supra*). Rabbit intestinal brush border membrane vesicles also exhibit Na+/nucleoside cotransport (Jarvis, *Biochim. Biophys. Acta.* 979:132–138 (1989)), but this appears to be a different gene product because SNST1 mRNA was not found in the intestinal mucosa (FIG. 1). SNST1 was abundantly expressed in the heart and so it may play a role in the physiological action of adenosine, which regulates cardiac contractility (Belardinelli et al., *Prog. Cardiovasc. Diseases* 32:73–97 (1989)).

EXAMPLE 2

This example describes the identification and use of specific inhibitors of SNST1.

Phloridzin, a specific inhibitor of Na+/glucose cotransport also inhibits Na+/nucleoside cotransport in the kidney brush border (Lee et al. *Am. J. Physiol.* 258:F1203–F1210 (1990)), which may reflect the evolutionary relationship between the two transport systems.

Uptake of radiolabeled nucleosides into *Xenopus* oocytes was measured in the presence or absence of Na+ as described above in Example 1, and in the presence and absence of 1 mM phloridzin (Sigma, St. Louis, Mo.). The expressed Na+/nucleoside cotransporter was 87% (n=2) inhibited by 1 mM phloridzin.

Although not wishing to be bound by any theory, phloridzin may inhibit SNST1 in the same manner as it inhibits SGLT1, i.e. the sugar residue competes for the nucleoside active site.

Phloridzin analogs such as phloretin-ribosides are expected to be more effective inhibitors of nucleoside transport because ribose should interact more specifically with the nucleoside active site. The position of the hydroxyl residues on the A and B rings of the phloretin moiety of phloridzin affects the potency of the inhibitor on glucose transport. For example the 4' glycoside is inactive and there is evidence that the 4' hydroxyl group is important in binding to the glucose transport protein (Diedrich et al., (1990), *supra*). Various phloridzin analogs are tested for inhibition of SNST1 using the procedure described above for testing inhibition by phloridzin. In these experiments, to investigate the parameters of inhibition, nucleoside concentration is varied by maintaining concentration of the phloridzin analog constant, and vice versa.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

---

We claim:

1. Isolated cDNA encoding the amino acid sequence shown in FIG. 2.

* * * * *

UNITED STATES PATENT AND TRADEMARK OFFICE
CERTIFICATE OF CORRECTION

PATENT NO. : 5,410,031

DATED : April 25, 1995

INVENTOR(S) : Wright et al.

It is certified that error appears in the above-identified patent and that said Letters Patent is hereby corrected as shown below:

In column 14, line 52, delete "." after the word "initiation";

In column 32, line 57, claim 1, insert --(Seq. ID NO:1)-- after the word "FIG. 2.".

Signed and Sealed this

Fourth Day of June, 1996

Attest:

BRUCE LEHMAN

Attesting Officer     Commissioner of Patents and Trademarks